(12) United States Patent  
Rothstein

(10) Patent No.: US 8,668,704 B2
(45) Date of Patent: Mar. 11, 2014

(54) MEDICAL CLIP WITH TINES, SYSTEM AND METHOD OF USING SAME

(75) Inventor: Paul Rothstein, Elk River, MN (US)

(73) Assignee: Medtronic, Inc., Minneapolis, MN (US)

( * ) Notice: Subject to any disclaimer, the term of this patent is extended or adjusted under 35 U.S.C. 154(b) by 796 days.

(21) Appl. No.: 12/429,366

(22) Filed: Apr. 24, 2009

(65) Prior Publication Data

US 2010/0274267 A1  Oct. 28, 2010

(51) Int. Cl.
 *A61B 17/08* (2006.01)
(52) U.S. Cl.
 USPC .......................................... 606/151; 606/142
(58) Field of Classification Search
 USPC ......... 606/139, 142, 143, 144, 148, 151, 155, 606/157, 158, 215, 216, 219, 220, 221
 See application file for complete search history.

(56) References Cited

U.S. PATENT DOCUMENTS

| | | | |
|---|---|---|---|
| 43,098 A | 6/1864 | Cooper | |
| 636,728 A | 11/1899 | Kindel | |
| 655,190 A | 8/1900 | Bramson | |
| 1,087,186 A | 2/1914 | Scholfield | |
| 1,167,014 A | 1/1916 | O'Brien | |
| 1,539,221 A | 5/1925 | Tennant | |
| 1,583,271 A | 5/1926 | Biro | |
| 1,625,602 A | 4/1927 | Gould et al. | |
| 1,867,624 A | 7/1932 | Hoffman | |
| 2,201,610 A | 5/1940 | Dawson, Jr. | |
| 2,240,330 A | 4/1941 | Flagg et al. | |
| 2,256,382 A | 9/1941 | Dole | |
| 2,264,679 A | 12/1941 | Ravel | |
| 2,413,142 A | 12/1946 | Jones et al. | |
| 2,430,293 A | 11/1947 | Howells | |
| 2,505,358 A | 4/1950 | Gusberg et al. | |
| 2,516,710 A | 7/1950 | Mascolo | |
| 2,715,486 A | 8/1955 | Marcoff-Moghadam et al. | |
| 2,890,519 A | 6/1959 | Storz, Jr. | |
| 2,940,452 A | 6/1960 | Smialowski | |
| 3,055,689 A | 9/1962 | Jorgensen | |
| 3,057,355 A | 10/1962 | Smialowski et al. | |
| 3,082,426 A | 3/1963 | Miles | |
| 3,143,742 A | 8/1964 | Cromie | |
| 3,150,379 A | 9/1964 | Brown | |

(Continued)

FOREIGN PATENT DOCUMENTS

| DE | 219999 | 3/1910 |
|---|---|---|
| DE | 377052 | 6/1923 |

(Continued)

OTHER PUBLICATIONS

US 6,503,260, 01/2003, Schaller et al. (withdrawn).

*Primary Examiner* — Thomas McEvoy

(57) ABSTRACT

Device, system and method for drawing together patient tissue. A tether loop is coupled to a first end loop and a second end loop. The first end loop and the second end loop each have an end and are resiliently biased to coil when deployed from a delivery catheter. When positioned within the delivery catheter the first end loop and the second end loop become substantially linear. Upon deployment from the delivery catheter the end loops coil and the first end passes through a first piece of tissue while the second end passes through a second piece of tissue. Each piece of tissue is captured within the corresponding end loop, the coiling of each of which draws the two pieces of tissue together.

22 Claims, 10 Drawing Sheets

(56) References Cited

U.S. PATENT DOCUMENTS

| | | |
|---|---|---|
| 3,180,337 A | 4/1965 | Smialowksi |
| 3,249,104 A | 5/1966 | Hohnstein |
| 3,274,658 A | 9/1966 | Pile |
| 3,452,742 A | 7/1969 | Muller |
| 3,506,012 A | 4/1970 | Brown |
| 3,509,882 A | 5/1970 | Blake |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| 3,656,185 A | 4/1972 | Carpentier |
| RE27,391 E | 6/1972 | Merser |
| 3,753,438 A | 8/1973 | Wood et al. |
| 3,776,237 A | 12/1973 | Hill et al. |
| 3,786,816 A | 1/1974 | Wolvek |
| 3,802,438 A | 4/1974 | Wolvek |
| 3,825,009 A | 7/1974 | Williams |
| 3,837,345 A | 9/1974 | Matar |
| 3,874,388 A | 4/1975 | King et al. |
| 3,875,648 A | 4/1975 | Bone |
| 3,905,403 A | 9/1975 | Smith et al. |
| 3,908,662 A | 9/1975 | Razgulov et al. |
| 3,910,281 A | 10/1975 | Kletshka et al. |
| 3,958,576 A | 5/1976 | Komiya |
| 3,976,079 A | 8/1976 | Samuels et al. |
| 3,995,619 A | 12/1976 | Glatzer |
| 4,006,747 A | 2/1977 | Kronenthal et al. |
| 4,018,228 A | 4/1977 | Goosen |
| 4,038,725 A | 8/1977 | Keefe |
| 4,042,979 A | 8/1977 | Angell |
| 4,073,179 A | 2/1978 | Hickey et al. |
| 4,103,690 A | 8/1978 | Harris |
| 4,111,206 A | 9/1978 | Vishnevsky et al. |
| 4,129,059 A | 12/1978 | Van Eck |
| 4,140,125 A | 2/1979 | Smith |
| 4,170,990 A | 10/1979 | Baumgart et al. |
| 4,185,636 A | 1/1980 | Gabbay et al. |
| 4,192,315 A | 3/1980 | Hilzinger et al. |
| 4,214,587 A | 7/1980 | Sakura, Jr. |
| 4,217,902 A | 8/1980 | March |
| 4,243,048 A | 1/1981 | Griffin |
| 4,324,248 A | 4/1982 | Perlin |
| 4,345,601 A | 8/1982 | Fukuda |
| 4,352,358 A | 10/1982 | Angelchik |
| 4,366,819 A | 1/1983 | Kaster |
| 4,396,139 A | 8/1983 | Hall et al. |
| 4,416,266 A | 11/1983 | Baucom |
| 4,456,017 A | 6/1984 | Miles |
| 4,465,071 A | 8/1984 | Samuels et al. |
| 4,470,415 A | 9/1984 | Wozniak |
| 4,470,533 A | 9/1984 | Schuler |
| 4,474,181 A | 10/1984 | Schenck |
| 4,485,816 A | 12/1984 | Krumme |
| 4,492,229 A | 1/1985 | Grunwald |
| 4,522,207 A | 6/1985 | Klieman et al. |
| 4,523,592 A | 6/1985 | Daniel |
| 4,532,927 A | 8/1985 | Miksza, Jr. |
| 4,535,764 A | 8/1985 | Ebert |
| 4,549,545 A | 10/1985 | Levy |
| 4,553,542 A | 11/1985 | Schenck et al. |
| 4,576,605 A | 3/1986 | Kaidash et al. |
| 4,586,502 A | 5/1986 | Bedi et al. |
| 4,586,503 A | 5/1986 | Kirsch et al. |
| 4,593,693 A | 6/1986 | Schenck |
| 4,595,007 A | 6/1986 | Mericle |
| 4,612,932 A | 9/1986 | Caspar et al. |
| 4,622,970 A | 11/1986 | Wozniak |
| 4,624,255 A | 11/1986 | Schenck et al. |
| 4,637,380 A | 1/1987 | Orejola |
| 4,641,652 A | 2/1987 | Hutterer et al. |
| 4,665,906 A | 5/1987 | Jervis |
| 4,665,917 A | 5/1987 | Clanton et al. |
| 4,683,895 A | 8/1987 | Pohndorf |
| 4,706,362 A | 11/1987 | Strausburg |
| 4,719,917 A | 1/1988 | Barrows et al. |
| 4,719,924 A | 1/1988 | Crittenden et al. |
| 4,730,615 A | 3/1988 | Sutherland et al. |
| 4,732,151 A | 3/1988 | Jones |
| 4,809,695 A | 3/1989 | Gwathmey et al. |
| 4,820,298 A | 4/1989 | Leveen et al. |
| 4,844,318 A | 7/1989 | Kunreuther |
| 4,873,975 A | 10/1989 | Walsh et al. |
| 4,890,615 A | 1/1990 | Caspari et al. |
| 4,896,668 A | 1/1990 | Popoff et al. |
| 4,899,744 A | 2/1990 | Fujitsuka et al. |
| 4,901,721 A | 2/1990 | Hakki |
| 4,923,461 A | 5/1990 | Caspari et al. |
| 4,924,866 A | 5/1990 | Yoon |
| 4,926,860 A | 5/1990 | Stice et al. |
| 4,929,240 A | 5/1990 | Kirsch et al. |
| 4,930,674 A | 6/1990 | Barak |
| 4,932,955 A | 6/1990 | Merz et al. |
| 4,935,027 A | 6/1990 | Yoon |
| 4,950,015 A | 8/1990 | Nejib et al. |
| 4,950,283 A | 8/1990 | Dzubow et al. |
| 4,950,285 A | 8/1990 | Wilk |
| 4,957,498 A | 9/1990 | Caspari et al. |
| 4,983,176 A | 1/1991 | Cushman et al. |
| 4,990,152 A | 2/1991 | Yoon |
| 4,991,567 A | 2/1991 | McCuen, II et al. |
| 4,994,069 A | 2/1991 | Ritchart et al. |
| 4,997,439 A | 3/1991 | Chen |
| 5,002,550 A | 3/1991 | Li |
| 5,002,562 A | 3/1991 | Oberlander |
| 5,002,563 A | 3/1991 | Pyka et al. |
| 5,007,920 A | 4/1991 | Torre |
| 5,011,481 A | 4/1991 | Myers et al. |
| 5,020,713 A | 6/1991 | Kunreuther |
| 5,026,379 A | 6/1991 | Yoon |
| 5,032,127 A | 7/1991 | Frazee et al. |
| 5,035,692 A | 7/1991 | Lyon et al. |
| 5,035,702 A | 7/1991 | Taheri |
| 5,042,707 A | 8/1991 | Taheri |
| 5,047,047 A | 9/1991 | Yoon |
| 5,053,047 A | 10/1991 | Yoon |
| 5,064,431 A | 11/1991 | Gilbertson et al. |
| 5,074,874 A | 12/1991 | Yoon et al. |
| 5,088,692 A | 2/1992 | Weiler |
| 5,100,418 A | 3/1992 | Yoon et al. |
| 5,100,421 A | 3/1992 | Christoudias |
| 5,104,407 A | 4/1992 | Lam et al. |
| 5,119,983 A | 6/1992 | Green et al. |
| 5,123,913 A | 6/1992 | Wilk et al. |
| 5,127,413 A | 7/1992 | Ebert |
| 5,129,913 A | 7/1992 | Ruppert |
| 5,152,769 A | 10/1992 | Baber |
| 5,154,189 A | 10/1992 | Oberlander |
| 5,158,566 A | 10/1992 | Pianetti |
| 5,171,250 A | 12/1992 | Yoon |
| 5,171,252 A | 12/1992 | Friedland |
| 5,174,087 A | 12/1992 | Bruno |
| 5,178,634 A | 1/1993 | Ramos Martinez |
| 5,192,294 A | 3/1993 | Blake, III |
| 5,196,022 A | 3/1993 | Bilweis |
| 5,201,880 A | 4/1993 | Wright et al. |
| 5,207,694 A | 5/1993 | Broome |
| 5,217,027 A | 6/1993 | Hermens |
| 5,219,358 A | 6/1993 | Bendel et al. |
| 5,221,259 A | 6/1993 | Weldon et al. |
| 5,222,961 A | 6/1993 | Nakao et al. |
| 5,222,976 A | 6/1993 | Yoon |
| 5,234,447 A | 8/1993 | Kaster et al. |
| 5,236,440 A | 8/1993 | Hlavacek |
| 5,242,456 A | 9/1993 | Nash et al. |
| 5,242,457 A | 9/1993 | Akopov et al. |
| 5,246,443 A | 9/1993 | Mai |
| 5,250,053 A | 10/1993 | Snyder |
| 5,258,011 A | 11/1993 | Drews |
| 5,261,917 A | 11/1993 | Hasson et al. |
| 5,269,783 A | 12/1993 | Sander |
| 5,269,809 A | 12/1993 | Hayhurst et al. |
| 5,282,825 A | 2/1994 | Muck et al. |
| 5,290,289 A | 3/1994 | Sanders et al. |
| 5,304,117 A | 4/1994 | Wilk |

(56) References Cited

U.S. PATENT DOCUMENTS

| | | |
|---|---|---|
| 5,304,204 A | 4/1994 | Bregen |
| 5,306,296 A | 4/1994 | Wright et al. |
| 5,312,436 A | 5/1994 | Coffey et al. |
| 5,314,468 A | 5/1994 | Ramos Martinez |
| 5,330,503 A | 7/1994 | Yoon |
| 5,334,196 A | 8/1994 | Scott et al. |
| 5,336,233 A | 8/1994 | Chen |
| 5,336,239 A | 8/1994 | Gimpelson |
| 5,346,459 A | 9/1994 | Allen |
| 5,350,420 A | 9/1994 | Cosgrove et al. |
| 5,353,804 A | 10/1994 | Kornberg et al. |
| 5,355,897 A | 10/1994 | Pietrafitta et al. |
| 5,356,424 A | 10/1994 | Buzerak et al. |
| 5,364,406 A | 11/1994 | Sewell, Jr. |
| 5,366,459 A | 11/1994 | Yoon |
| 5,366,462 A | 11/1994 | Kaster et al. |
| 5,366,479 A | 11/1994 | McGarry et al. |
| 5,374,268 A | 12/1994 | Sander |
| 5,376,096 A | 12/1994 | Foster |
| 5,382,259 A | 1/1995 | Phelps et al. |
| 5,383,904 A | 1/1995 | Totakura et al. |
| 5,387,227 A | 2/1995 | Grice |
| 5,403,331 A | 4/1995 | Chesterfield et al. |
| 5,403,333 A | 4/1995 | Kaster et al. |
| 5,403,338 A | 4/1995 | Milo |
| 5,403,346 A | 4/1995 | Loeser |
| 5,413,584 A | 5/1995 | Schulze |
| 5,417,684 A | 5/1995 | Jackson et al. |
| 5,417,700 A | 5/1995 | Egan |
| 5,423,821 A | 6/1995 | Pasque |
| 5,431,666 A | 7/1995 | Sauer et al. |
| 5,437,680 A | 8/1995 | Yoon |
| 5,437,681 A | 8/1995 | Meade et al. |
| 5,437,685 A | 8/1995 | Blasnik |
| 5,439,479 A | 8/1995 | Shichman et al. |
| 5,445,167 A | 8/1995 | Yoon et al. |
| 5,445,644 A | 8/1995 | Pietrafitta et al. |
| 5,450,860 A | 9/1995 | O'Connor |
| 5,451,231 A | 9/1995 | Rabenau et al. |
| 5,452,733 A | 9/1995 | Sterman et al. |
| 5,454,834 A | 10/1995 | Boebel et al. |
| 5,456,246 A | 10/1995 | Schmieding et al. |
| 5,462,561 A | 10/1995 | Voda |
| 5,474,557 A | 12/1995 | Mai |
| 5,480,405 A | 1/1996 | Yoon |
| 5,486,187 A | 1/1996 | Schenck |
| 5,486,197 A | 1/1996 | Le et al. |
| 5,488,958 A | 2/1996 | Topel et al. |
| 5,496,334 A | 3/1996 | Klundt et al. |
| 5,499,990 A | 3/1996 | Schulken et al. |
| 5,500,000 A | 3/1996 | Feagin et al. |
| 5,527,342 A | 6/1996 | Pietrzak et al. |
| 5,533,236 A | 7/1996 | Tseng |
| 5,538,509 A | 7/1996 | Dunlap et al. |
| 5,545,214 A | 8/1996 | Stevens |
| 5,549,619 A | 8/1996 | Peters et al. |
| 5,552,884 A | 9/1996 | Li et al. |
| 5,556,411 A | 9/1996 | Taoda et al. |
| 5,562,685 A | 10/1996 | Mollenauer et al. |
| 5,569,205 A | 10/1996 | Hart et al. |
| 5,569,274 A | 10/1996 | Rapacki et al. |
| 5,569,301 A | 10/1996 | Granger et al. |
| 5,571,119 A | 11/1996 | Atala |
| 5,571,175 A | 11/1996 | Vanney et al. |
| 5,582,616 A | 12/1996 | Bolduc et al. |
| 5,582,619 A | 12/1996 | Ken |
| 5,584,879 A | 12/1996 | Reimold et al. |
| 5,586,983 A | 12/1996 | Sanders et al. |
| 5,591,179 A | 1/1997 | Edelstein |
| 5,593,414 A | 1/1997 | Shipp et al. |
| 5,593,424 A | 1/1997 | Northrup, III |
| 5,597,378 A | 1/1997 | Jervis |
| 5,601,571 A | 2/1997 | Moss |
| 5,601,572 A | 2/1997 | Middleman et al. |
| 5,601,600 A | 2/1997 | Ton |
| 5,603,718 A | 2/1997 | Xu |
| 5,609,608 A | 3/1997 | Benett et al. |
| 5,628,757 A | 5/1997 | Hasson |
| 5,630,540 A | 5/1997 | Blewett |
| 5,632,752 A | 5/1997 | Buelna |
| 5,632,753 A | 5/1997 | Loeser |
| 5,643,295 A | 7/1997 | Yoon |
| 5,643,305 A | 7/1997 | Al-Tameem |
| 5,645,568 A | 7/1997 | Chervitz et al. |
| 5,653,716 A | 8/1997 | Malo et al. |
| 5,653,718 A | 8/1997 | Yoon |
| 5,658,312 A | 8/1997 | Green et al. |
| 5,660,186 A | 8/1997 | Bachir |
| 5,665,109 A | 9/1997 | Yoon |
| 5,669,918 A | 9/1997 | Balazs et al. |
| 5,676,670 A | 10/1997 | Kim |
| 5,683,417 A | 11/1997 | Cooper |
| 5,690,662 A | 11/1997 | Chiu et al. |
| 5,695,504 A | 12/1997 | Gifford, III et al. |
| 5,695,505 A | 12/1997 | Yoon |
| 5,697,913 A | 12/1997 | Sierocuk et al. |
| 5,697,943 A | 12/1997 | Sauer et al. |
| 5,700,270 A | 12/1997 | Peyser et al. |
| 5,700,271 A | 12/1997 | Whitfield et al. |
| 5,702,412 A | 12/1997 | Popov et al. |
| 5,707,362 A | 1/1998 | Yoon |
| 5,707,380 A | 1/1998 | Hinchliffe et al. |
| 5,709,693 A | 1/1998 | Taylor |
| 5,709,695 A | 1/1998 | Northrup, III |
| 5,715,987 A | 2/1998 | Kelley et al. |
| 5,720,755 A | 2/1998 | Dakov |
| 5,725,539 A | 3/1998 | Matern |
| 5,725,542 A | 3/1998 | Yoon |
| 5,728,135 A | 3/1998 | Bregen et al. |
| 5,732,872 A | 3/1998 | Bolduc et al. |
| 5,735,290 A | 4/1998 | Sterman et al. |
| 5,746,753 A | 5/1998 | Sullivan et al. |
| 5,755,778 A | 5/1998 | Kleshinski |
| 5,766,189 A | 6/1998 | Matsuno |
| 5,769,870 A | 6/1998 | Salahieh et al. |
| 5,779,718 A | 7/1998 | Green et al. |
| 5,782,397 A | 7/1998 | Koukline |
| 5,782,844 A | 7/1998 | Yoon et al. |
| 5,797,920 A | 8/1998 | Kim |
| 5,797,933 A | 8/1998 | Snow et al. |
| 5,797,934 A | 8/1998 | Rygaard |
| 5,797,960 A | 8/1998 | Stevens et al. |
| 5,799,661 A | 9/1998 | Boyd et al. |
| 5,799,857 A | 9/1998 | Robertson et al. |
| 5,810,848 A | 9/1998 | Hayhurst |
| 5,810,851 A | 9/1998 | Yoon |
| 5,810,853 A | 9/1998 | Yoon |
| 5,810,882 A | 9/1998 | Bolduc et al. |
| 5,817,113 A | 10/1998 | Gifford, III et al. |
| 5,820,631 A | 10/1998 | Nobles |
| 5,824,002 A | 10/1998 | Gentelia et al. |
| 5,824,008 A | 10/1998 | Bolduc et al. |
| 5,827,265 A | 10/1998 | Glinsky et al. |
| 5,827,316 A | 10/1998 | Young et al. |
| 5,830,221 A | 11/1998 | Stein et al. |
| 5,830,222 A | 11/1998 | Makower |
| 5,833,698 A | 11/1998 | Hinchliffe et al. |
| 5,849,019 A | 12/1998 | Yoon |
| 5,851,216 A | 12/1998 | Allen |
| 5,855,614 A | 1/1999 | Stevens et al. |
| 5,868,702 A | 2/1999 | Stevens et al. |
| 5,868,763 A | 2/1999 | Spence et al. |
| 5,871,528 A | 2/1999 | Camps et al. |
| 5,879,371 A | 3/1999 | Gardiner et al. |
| 5,881,943 A | 3/1999 | Heck et al. |
| 5,882,340 A | 3/1999 | Yoon |
| 5,891,130 A | 4/1999 | Palermo et al. |
| 5,891,160 A | 4/1999 | Williamson, IV et al. |
| 5,893,369 A | 4/1999 | LeMole |
| 5,893,865 A | 4/1999 | Swindle et al. |
| 5,893,886 A | 4/1999 | Zegdi et al. |
| 5,895,394 A | 4/1999 | Kienzle et al. |
| 5,904,697 A | 5/1999 | Gifford, III et al. |
| 5,908,428 A | 6/1999 | Scirica et al. |

(56) References Cited

U.S. PATENT DOCUMENTS

| | | |
|---|---|---|
| 5,911,352 A | 6/1999 | Racenet et al. |
| 5,919,207 A | 7/1999 | Taheri |
| 5,931,842 A | 8/1999 | Goldsteen et al. |
| 5,941,434 A | 8/1999 | Green |
| 5,941,442 A | 8/1999 | Geiste et al. |
| 5,941,888 A | 8/1999 | Wallace et al. |
| 5,941,908 A | 8/1999 | Goldsteen et al. |
| 5,944,730 A | 8/1999 | Nobles et al. |
| 5,951,576 A | 9/1999 | Wakabayashi |
| 5,951,600 A | 9/1999 | Lemelson |
| 5,954,735 A | 9/1999 | Rygaard |
| 5,957,363 A | 9/1999 | Heck |
| 5,957,938 A | 9/1999 | Zhu et al. |
| 5,957,940 A | 9/1999 | Tanner et al. |
| 5,961,481 A | 10/1999 | Sterman et al. |
| 5,961,539 A | 10/1999 | Northrup, III et al. |
| 5,964,772 A | 10/1999 | Bolduc et al. |
| 5,964,782 A | 10/1999 | Lafontaine et al. |
| 5,972,024 A | 10/1999 | Northrup, III et al. |
| 5,976,159 A | 11/1999 | Bolduc et al. |
| 5,976,161 A | 11/1999 | Kirsch et al. |
| 5,976,164 A | 11/1999 | Bencini et al. |
| 5,976,178 A | 11/1999 | Goldsteen et al. |
| 5,984,917 A | 11/1999 | Fleischman et al. |
| 5,984,959 A | 11/1999 | Robertson et al. |
| 5,989,242 A | 11/1999 | Saadat et al. |
| 5,989,268 A | 11/1999 | Pugsley, Jr. et al. |
| 5,989,276 A | 11/1999 | Houser et al. |
| 5,989,278 A | 11/1999 | Mueller |
| 5,993,468 A | 11/1999 | Rygaard |
| 5,997,556 A | 12/1999 | Tanner |
| 6,001,110 A | 12/1999 | Adams |
| 6,007,544 A | 12/1999 | Kim |
| 6,010,531 A | 1/2000 | Donlon et al. |
| 6,013,084 A | 1/2000 | Ken et al. |
| 6,022,367 A | 2/2000 | Sherts |
| 6,024,748 A | 2/2000 | Manzo et al. |
| 6,032,849 A | 3/2000 | Mastri et al. |
| 6,033,419 A | 3/2000 | Hamblin, Jr. et al. |
| 6,036,699 A | 3/2000 | Andreas et al. |
| 6,036,703 A | 3/2000 | Evans et al. |
| 6,036,710 A | 3/2000 | McGarry et al. |
| 6,042,607 A | 3/2000 | Williamson, IV et al. |
| 6,056,751 A | 5/2000 | Fenton, Jr. |
| 6,063,070 A | 5/2000 | Eder |
| 6,066,148 A | 5/2000 | Rygaard |
| 6,074,401 A | 6/2000 | Gardiner et al. |
| 6,074,418 A | 6/2000 | Buchanan et al. |
| 6,077,291 A | 6/2000 | Das |
| 6,080,114 A | 6/2000 | Russin |
| 6,083,237 A | 7/2000 | Huitema et al. |
| 6,106,538 A | 8/2000 | Shiber |
| 6,110,188 A | 8/2000 | Narciso, Jr. |
| 6,113,611 A | 9/2000 | Allen et al. |
| 6,113,612 A | 9/2000 | Swanson et al. |
| 6,120,524 A | 9/2000 | Taheri |
| 6,132,438 A | 10/2000 | Fleischman et al. |
| 6,139,540 A | 10/2000 | Rost et al. |
| 6,143,004 A | 11/2000 | Davis et al. |
| 6,149,658 A | 11/2000 | Gardiner et al. |
| 6,152,935 A | 11/2000 | Kammerer et al. |
| 6,152,937 A | 11/2000 | Peterson et al. |
| 6,159,165 A | 12/2000 | Ferrera et al. |
| 6,159,225 A | 12/2000 | Makower |
| 6,165,183 A | 12/2000 | Kuehn et al. |
| 6,165,185 A | 12/2000 | Shennib et al. |
| 6,171,320 B1 | 1/2001 | Monassevitch |
| 6,171,321 B1 | 1/2001 | Gifford, III et al. |
| 6,176,413 B1 | 1/2001 | Heck et al. |
| 6,176,864 B1 | 1/2001 | Chapman |
| 6,179,840 B1 | 1/2001 | Bowman |
| 6,179,848 B1 | 1/2001 | Solem |
| 6,179,849 B1 | 1/2001 | Yencho et al. |
| 6,183,512 B1 | 2/2001 | Howanec, Jr. et al. |
| 6,190,373 B1 | 2/2001 | Palermo et al. |
| 6,193,733 B1 | 2/2001 | Adams |
| 6,193,734 B1 | 2/2001 | Bolduc et al. |
| 6,197,037 B1 | 3/2001 | Hair |
| 6,217,611 B1 | 4/2001 | Klostermeyer |
| 6,221,083 B1 | 4/2001 | Mayer |
| 6,241,738 B1 | 6/2001 | Dereume |
| 6,241,741 B1 | 6/2001 | Duhaylongsod et al. |
| 6,248,117 B1 | 6/2001 | Blatter |
| 6,250,308 B1 | 6/2001 | Cox |
| 6,254,615 B1 | 7/2001 | Bolduc et al. |
| 6,269,819 B1 | 8/2001 | Oz et al. |
| 6,280,460 B1 | 8/2001 | Bolduc et al. |
| 6,283,979 B1 | 9/2001 | Mers Kelly et al. |
| 6,296,622 B1 | 10/2001 | Kurz et al. |
| 6,296,656 B1 | 10/2001 | Bolduc et al. |
| 6,306,141 B1 | 10/2001 | Jervis |
| 6,332,893 B1 | 12/2001 | Mortier et al. |
| 6,346,074 B1 | 2/2002 | Roth |
| 6,346,112 B2 | 2/2002 | Adams |
| 6,350,269 B1 | 2/2002 | Shipp et al. |
| 6,352,543 B1 | 3/2002 | Cole |
| 6,358,258 B1 | 3/2002 | Arcia et al. |
| 6,361,559 B1 | 3/2002 | Houser et al. |
| 6,368,348 B1 | 4/2002 | Gabbay |
| 6,371,964 B1 | 4/2002 | Vargas et al. |
| 6,387,105 B1 | 5/2002 | Gifford, III et al. |
| 6,391,038 B2 | 5/2002 | Vargas et al. |
| 6,402,764 B1 | 6/2002 | Hendricksen et al. |
| 6,406,492 B1 | 6/2002 | Lytle |
| 6,406,493 B1 | 6/2002 | Tu et al. |
| 6,409,739 B1 | 6/2002 | Nobles et al. |
| 6,409,758 B2 | 6/2002 | Stobie et al. |
| 6,416,527 B1 | 7/2002 | Berg et al. |
| 6,418,597 B1 | 7/2002 | Deschenes et al. |
| 6,419,658 B1 | 7/2002 | Restelli et al. |
| 6,419,681 B1 | 7/2002 | Vargas et al. |
| 6,419,695 B1 | 7/2002 | Gabbay |
| 6,425,900 B1 | 7/2002 | Knodel et al. |
| 6,428,550 B1 | 8/2002 | Vargas et al. |
| 6,428,555 B1 | 8/2002 | Koster, Jr. |
| 6,451,048 B1 | 9/2002 | Berg et al. |
| 6,461,320 B1 | 10/2002 | Yencho et al. |
| 6,475,222 B1 | 11/2002 | Berg et al. |
| 6,478,804 B2 | 11/2002 | Vargas et al. |
| 6,485,496 B1 | 11/2002 | Suyker et al. |
| 6,491,707 B2 | 12/2002 | Makower et al. |
| 6,497,671 B2 | 12/2002 | Ferrera et al. |
| 6,497,710 B2 | 12/2002 | Yencho et al. |
| 6,514,265 B2 | 2/2003 | Ho et al. |
| 6,517,558 B2 | 2/2003 | Gittings et al. |
| 6,524,338 B1 | 2/2003 | Gundry |
| 6,533,812 B2 | 3/2003 | Swanson et al. |
| 6,537,288 B2 | 3/2003 | Vargas et al. |
| 6,547,799 B2 | 4/2003 | Hess et al. |
| 6,551,332 B1 | 4/2003 | Nguyen et al. |
| 6,562,053 B2 | 5/2003 | Schulze |
| 6,575,985 B2 | 6/2003 | Knight et al. |
| 6,589,255 B2 | 7/2003 | Schulze et al. |
| 6,607,541 B1 | 8/2003 | Gardiner et al. |
| 6,607,542 B1 | 8/2003 | Wild |
| 6,613,059 B2 | 9/2003 | Schaller et al. |
| 6,629,988 B2 | 10/2003 | Weadock |
| 6,635,214 B2 | 10/2003 | Rapacki et al. |
| 6,641,593 B1 | 11/2003 | Schaller et al. |
| 6,648,900 B2 | 11/2003 | Fleischman et al. |
| 6,651,670 B2 | 11/2003 | Rapacki et al. |
| 6,651,672 B2 | 11/2003 | Roth |
| 6,652,540 B1 | 11/2003 | Cole et al. |
| 6,652,541 B1 | 11/2003 | Vargas et al. |
| 6,660,015 B1 | 12/2003 | Berg et al. |
| 6,682,540 B1 | 1/2004 | Sancoff et al. |
| 6,695,859 B1 | 2/2004 | Golden et al. |
| 6,702,826 B2 | 3/2004 | Liddicoat et al. |
| 6,704,401 B2 | 3/2004 | Piepho et al. |
| 6,709,442 B2 | 3/2004 | Miller et al. |
| 6,712,829 B2 | 3/2004 | Schulze |
| 6,719,768 B1 | 4/2004 | Cole et al. |
| 6,743,243 B1 | 6/2004 | Roy et al. |
| 6,749,622 B2 | 6/2004 | McGuckin, Jr. et al. |

(56) References Cited

U.S. PATENT DOCUMENTS

| | | |
|---|---|---|
| 6,776,782 B2 | 8/2004 | Schulze |
| 6,776,784 B2 | 8/2004 | Ginn |
| 6,776,785 B1 | 8/2004 | Yencho et al. |
| 6,802,847 B1 | 10/2004 | Carson et al. |
| 6,821,286 B1 | 11/2004 | Carranza et al. |
| 6,869,444 B2 | 3/2005 | Gabbay |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,945,980 B2 | 9/2005 | Nguyen et al. |
| 6,955,679 B1 | 10/2005 | Hendricksen et al. |
| 6,960,221 B2 | 11/2005 | Ho et al. |
| 6,979,337 B2 | 12/2005 | Kato |
| 6,979,338 B1 | 12/2005 | Loshakove et al. |
| 7,022,131 B1 | 4/2006 | Derowe et al. |
| 7,056,330 B2 | 6/2006 | Gayton |
| 7,063,711 B1 | 6/2006 | Loshakove et al. |
| 7,070,618 B2 | 7/2006 | Streeter |
| 7,182,769 B2 | 2/2007 | Ainsworth et al. |
| 7,220,268 B2 | 5/2007 | Blatter |
| 2001/0018592 A1 | 8/2001 | Schaller et al. |
| 2001/0018593 A1 | 8/2001 | Nguyen et al. |
| 2001/0018611 A1 | 8/2001 | Solem et al. |
| 2001/0021856 A1 | 9/2001 | Bolduc et al. |
| 2001/0047181 A1 | 11/2001 | Ho et al. |
| 2002/0010490 A1 | 1/2002 | Schaller et al. |
| 2002/0042623 A1 | 4/2002 | Blatter et al. |
| 2002/0082614 A1 | 6/2002 | Logan et al. |
| 2002/0099395 A1 | 7/2002 | Acampora et al. |
| 2002/0151916 A1 | 10/2002 | Muramatsu et al. |
| 2002/0165561 A1 | 11/2002 | Ainsworth et al. |
| 2002/0173803 A1 | 11/2002 | Ainsworth et al. |
| 2003/0074012 A1 | 4/2003 | Nguyen et al. |
| 2003/0078603 A1 | 4/2003 | Schaller et al. |
| 2003/0083742 A1 | 5/2003 | Spence et al. |
| 2003/0093118 A1 | 5/2003 | Ho et al. |
| 2003/0125755 A1 | 7/2003 | Schaller et al. |
| 2003/0144694 A1* | 7/2003 | Chanduszko et al. ........ 606/213 |
| 2003/0191481 A1 | 10/2003 | Nguyen et al. |
| 2003/0195531 A1 | 10/2003 | Gardiner et al. |
| 2003/0199974 A1 | 10/2003 | Lee et al. |
| 2004/0050393 A1 | 3/2004 | Golden et al. |
| 2004/0068276 A1 | 4/2004 | Golden et al. |
| 2004/0102797 A1 | 5/2004 | Golden et al. |
| 2004/0111099 A1 | 6/2004 | Nguyen et al. |
| 2004/0138685 A1 | 7/2004 | Clague et al. |
| 2004/0176663 A1 | 9/2004 | Edoga et al. |
| 2004/0193259 A1 | 9/2004 | Gabbay |
| 2005/0004582 A1 | 1/2005 | Edoga et al. |
| 2005/0021054 A1 | 1/2005 | Ainsworth et al. |
| 2005/0043749 A1 | 2/2005 | Breton et al. |
| 2005/0065601 A1 | 3/2005 | Lee et al. |
| 2005/0070924 A1 | 3/2005 | Schaller et al. |
| 2005/0075659 A1 | 4/2005 | Realyvasquez et al. |
| 2005/0075667 A1 | 4/2005 | Schaller et al. |
| 2005/0080454 A1 | 4/2005 | Drews et al. |
| 2005/0101975 A1 | 5/2005 | Nguyen et al. |
| 2005/0107871 A1 | 5/2005 | Realyvasquez et al. |
| 2005/0119675 A1* | 6/2005 | Adams et al. ................. 606/151 |
| 2005/0131429 A1 | 6/2005 | Ho et al. |
| 2005/0165305 A1* | 7/2005 | Foerster et al. .............. 600/431 |
| 2005/0267572 A1 | 12/2005 | Schoon et al. |
| 2006/0004389 A1 | 1/2006 | Nguyen et al. |
| 2006/0253143 A1 | 11/2006 | Edoga et al. |
| 2006/0271081 A1 | 11/2006 | Realyvasquez |
| 2006/0293701 A1 | 12/2006 | Ainsworth et al. |
| 2007/0010835 A1 | 1/2007 | Breton et al. |
| 2007/0027461 A1 | 2/2007 | Gardiner et al. |
| 2007/0106313 A1 | 5/2007 | Golden et al. |
| 2007/0142848 A1 | 6/2007 | Ainsworth et al. |

FOREIGN PATENT DOCUMENTS

| | | |
|---|---|---|
| DE | 2703529 A1 | 8/1978 |
| DE | 3203410 A1 | 11/1982 |
| DE | 3227984 A1 | 2/1984 |
| DE | 3504202 A1 | 8/1985 |
| DE | 4133800 C1 | 1/1993 |
| DE | 4402058 C1 | 4/1995 |
| DE | 19547617 C1 | 9/1997 |
| DE | 19732234 A1 | 1/1999 |
| EP | 0072232 B1 | 2/1983 |
| EP | 0121362 B1 | 10/1984 |
| EP | 0122046 A1 | 10/1984 |
| EP | 0129441 B1 | 12/1984 |
| EP | 0130037 A1 | 1/1985 |
| EP | 0140557 A2 | 5/1985 |
| EP | 0326426 B1 | 8/1989 |
| EP | 0409569 B1 | 1/1991 |
| EP | 0419597 B1 | 4/1991 |
| EP | 0432692 A1 | 6/1991 |
| EP | 0478949 A1 | 4/1992 |
| EP | 0494636 B1 | 7/1992 |
| EP | 0537955 A2 | 4/1993 |
| EP | 0559429 B1 | 9/1993 |
| EP | 0598529 A2 | 5/1994 |
| EP | 0632999 A1 | 1/1995 |
| EP | 0641546 A1 | 3/1995 |
| EP | 0656191 A2 | 6/1995 |
| EP | 0687446 A2 | 12/1995 |
| EP | 0705568 B1 | 4/1996 |
| EP | 0705569 B1 | 4/1996 |
| EP | 0711532 A1 | 5/1996 |
| EP | 0734697 B1 | 10/1996 |
| EP | 0778005 A1 | 12/1996 |
| EP | 0815795 B1 | 1/1998 |
| GB | 2223410 A | 4/1990 |
| JP | 07308322 | 11/1995 |
| JP | 08336544 | 12/1996 |
| JP | 10337291 | 12/1998 |
| RU | 2110222 C1 | 5/1998 |
| SU | 577022 A1 | 10/1977 |
| SU | 1186199 A1 | 2/1983 |
| SU | 1456109 A1 | 2/1989 |
| SU | 1560133 A1 | 4/1990 |
| WO | 9006725 A1 | 6/1990 |
| WO | 9009149 A1 | 8/1990 |
| WO | 9014795 A2 | 12/1990 |
| WO | 9107916 A1 | 6/1991 |
| WO | 9108708 A1 | 6/1991 |
| WO | 9117712 A1 | 11/1991 |
| WO | 9205828 A1 | 4/1992 |
| WO | 9212676 A2 | 8/1992 |
| WO | 9222041 A2 | 12/1992 |
| WO | 9301750 A1 | 2/1993 |
| WO | 9415535 A1 | 7/1994 |
| WO | 9415537 A1 | 7/1994 |
| WO | 9600035 A1 | 1/1996 |
| WO | 9606565 A1 | 3/1996 |
| WO | 9638090 A1 | 12/1996 |
| WO | 9712555 A2 | 4/1997 |
| WO | 9716122 A1 | 5/1997 |
| WO | 9727898 A1 | 8/1997 |
| WO | 9728744 A1 | 8/1997 |
| WO | 9731575 A1 | 9/1997 |
| WO | 9732526 A1 | 9/1997 |
| WO | 9740754 A1 | 11/1997 |
| WO | 9742881 A1 | 11/1997 |
| WO | 9819636 A2 | 5/1998 |
| WO | 9830153 A1 | 7/1998 |
| WO | WO9830153 A1 | 7/1998 |
| WO | 9842262 A1 | 10/1998 |
| WO | 9848707 A1 | 11/1998 |
| WO | 9852475 A1 | 11/1998 |
| WO | 9907294 A1 | 2/1999 |
| WO | 9912484 A1 | 3/1999 |
| WO | 9915088 A1 | 4/1999 |
| WO | 9937218 A1 | 7/1999 |
| WO | 9962406 | 12/1999 |
| WO | 9962408 A1 | 12/1999 |

(56) References Cited

FOREIGN PATENT DOCUMENTS

| | | |
|---|---|---|
| WO | 9962409 | 12/1999 |
| WO | 9962415 A1 | 12/1999 |
| WO | 9963910 A1 | 12/1999 |
| WO | 9965409 A1 | 12/1999 |
| WO | 0003759 A2 | 1/2000 |
| WO | 0015144 A1 | 3/2000 |
| WO | 0059380 A2 | 10/2000 |
| WO | 0060995 A2 | 10/2000 |
| WO | 0064381 A2 | 11/2000 |
| WO | 0074603 A1 | 12/2000 |
| WO | 0119292 A1 | 3/2001 |
| WO | 0126557 A1 | 4/2001 |
| WO | 0126586 A1 | 4/2001 |
| WO | 0128432 A1 | 4/2001 |
| WO | 0154618 A | 8/2001 |
| WO | 0174254 A1 | 10/2001 |
| WO | 0213701 A1 | 2/2002 |
| WO | 0213702 A1 | 2/2002 |
| WO | 0230295 A1 | 4/2002 |
| WO | 0230298 A1 | 4/2002 |
| WO | 0234143 A1 | 5/2002 |
| WO | 02080779 A1 | 10/2002 |
| WO | 02080780 A1 | 10/2002 |
| WO | 02087425 A2 | 11/2002 |
| WO | 03053289 A1 | 7/2003 |
| WO | 03088875 A1 | 10/2003 |
| WO | 2005011468 A2 | 2/2005 |
| WO | 2005058170 A1 | 6/2005 |

\* cited by examiner

MEDICAL CLIP WITH TINES, SYSTEM AND METHOD OF USING SAME

FIELD

The present invention relates generally to devices, systems and methods of drawing patient tissue together, and in particular such devices, systems and methods of drawing patient tissue together using a medical clip.

BACKGROUND

In many circumstances and for many reasons, it is often beneficial to capture and draw together two or more pieces of tissue of a patient. The location of the tissue and the circumstances of the need to draw the pieces of tissue together have long resulted in a variety of different devices and methods for drawing the tissue together. Devices such as bandages, both self-adhesive and otherwise, clamps and stitches have been used to capture pieces of tissue and draw them together. Once tissue is drawn together, the natural healing abilities of the body may then allow the pieces of tissue to grow together, over time sealing a gap between the pieces of tissue such that the device is no longer needed. Alternatively, the pieces of tissue may be held together by the device indefinitely, or for a particular period of time.

But, dependent on the location of the tissue, certain devices and methods may be impractical to utilize. For instance, while stitches may lend themselves well to readily accessible patient tissue, such as skin and muscle tissue, relatively inaccessible tissue, such as that found in the organs of the patient, may be impractical to capture and draw together using stitches. As such, the use of stitches to treat a defect in a patient's heart may tend require a traumatic open heart procedure, and even then, because the interior of the heart still may not be readily accessible, the treatment of a defect inside the heart may still not be attainable with stitches. Thus, a common device and method for drawing together patient tissue may not be applicable for all situations, particularly those involving a defect in organs of the patient such as the heart.

One relatively common defect in the heart of newborn children, which may also be present in older children and in adults, is a patent foramen ovale ("PFO"). During the gestation of a fetus in the womb, blood is oxygenated not by the undeveloped lungs of the fetus, but rather by the placenta of the mother. However, the heart of the fetus nevertheless pumps the blood through the cardiovascular system and receives the blood from the cardiovascular system. As such, in order to avoid the undeveloped lungs of the fetus, various vessels and bypasses exist that operate only during gestation that divert the blood from the lungs. At birth these bypasses typically close and circulation occurs by way of the lungs as with a normally developed adult.

An opening between the right atrium and the left atrium called the foramen ovale is open during gestation to prevent transfer of blood from the right ventricle of the heart to the lungs during gestation. Upon birth, the child's inherent circulation creates pressure within the atrium which causes a flap of tissue to close over the foramen ovale. As the child matures, the flap of tissue develops into a permanent closure. However, in some children the flap of tissue does not close, either in whole or in part, over the entire foramen ovale, creating a patent foramen ovale. The continued existence of the foramen ovale results in continued diversion from the lungs of at least some of the child's blood, reducing the flow of oxygenated blood through the child's system, and potentially leading to serious complications to the health of the child.

It is recognized that although PFO may occur most prominently in children and, in particular, relatively newborn children, that the PFO may also occur or be present in older children and in adults.

Other cardiac defects are known to exist beyond patent foramen ovales. For instance, atrial-septal defects ("ASD") and ventricular-septal defects ("VSD") likewise sometimes occur and may be detrimental to the health of the person, e.g., a child. Historically, open heart surgery had been required to fix such defects. But open heart surgery carries with it serious and well-known and recognized risks to the well-being of the person, in addition to being expensive and a considerable burden on hospital resources.

Closure devices for treating heart defects, such as patent foramen ovales, have been developed.

U.S. Pat. No. 6,776,784, Ginn, Clip Apparatus For Closing Septal Defects and Methods of Use, (Core Medical, Inc.) discloses a device for closing a septal defect, such as a patent foramen ovale, includes a clip formed from a superelastic material that is inserted into a septum wall of a heart. The clip is advanced through a patient's vasculature, e.g., within a delivery apparatus, until the clip is disposed within a first chamber adjacent the septal defect. Tines of the clip are directed through a flap of tissue of the septal defect until the tines of the clip are disposed within a second opposing chamber. The clip then transforms into its relaxed state, wherein the tines of the clip engage with a surface of the second chamber, thereby substantially closing the septal opening.

U.S. Patent Application Publication No. US2007/0060858, Sogard et al, Defect Occlusion Apparatus, System and Method, discloses occluding a multiplicity of parallel membranes, such as found in a patent foramen ovale. The methods, apparatus, and systems include the use of a positioning device that can be seated on the limbus of the septum secundum. The positioning device includes a piercing member that can pierce the septum secundum and septum primum. The positioning device also includes a fastening member that can engage the septum secundum and septum primum to fasten the tissues and thereby occlude a patent foramen ovale.

U.S. Pat. No. 7,220,265, Chanduszko et al, Patent Foramen Ovale (PFO) Closure Method and Device, (NMT Medical, Inc.) discloses methods and devices for closing two overlapping layers of tissue in a mammalian heart, such as a patent foramen ovale. The closure devices may take a number of different forms and may be retrievable. In some embodiments, the closure devices may be delivered with a catheter capable of puncturing mammalian tissue. In some embodiments, a spring-like bioabsorbable polymer material are used, in one such embodiment as a "grappling hook", to embed in and draw together the pieces of tissue. In another embodiment, a suture is delivered, and an anchor forms a pre-determined shape and engages the septum secundum, closing the patent foramen ovale.

SUMMARY

Closure devices for treating patent foramen ovales have been developed that allow for the treatment of patent foramen ovales and other cardiac defects without conducting open heart surgery. Instead, the closure devices may be utilized to cure or treat cardiac defects by way of transveneous implantation. With the device placed in a sheath attached to a catheter small enough to pass through the blood vessels of the child and into the heart, the device may be deployed in the heart to treat the cardiac defect.

The device itself may be made of a number of joined loops. A pair of end loops may be coupled to a central tether loop. An end of each end loop may be sharpened to facilitate penetrating the cardiac tissue of the patient. When drawn into the sheath of the deployment catheter, the end loops may be straightened out to be approximately linear. Once the device is deployed the loops may be resiliently biased to form back into loops. During a transition from a relatively linear configuration to a coiled configuration, the sharpened end of the end loops may pass through cardiac tissue. In the case of the treatment of a patent foramen ovale, if the device is positioned adjoining the two flaps of tissue which did not automatically close together, at least one end may pass through each flap of tissue as the loops are formed. As the loops complete forming, the two flaps of tissue may be drawn together, either closing the foramen ovale altogether, or bringing the flaps of tissue in closer proximity of each other such that vascular pressure may ultimately bring the flaps of tissue together. As the patient matures flaps of tissue may grow together and the foramen ovale close permanently.

In an embodiment, a medical clip adapted to be used with a delivery catheter having a longitudinal axis and a lumen is disclosed. The medical clip comprises a tether loop, a first end loop having one end coupled to the tether loop and a first tip at an opposite end of the first end loop, the first end loop being resiliently biased to form a coil when the first end loop is free from being constrained by the lumen of the delivery catheter, and a second end loop having one end coupled to the tether loop and a second tip at an opposite end of the second end loop, the second end loop being resiliently biased to form a coil when the second end loop is free from being constrained by the lumen of the delivery catheter. Each of the first end loop and the second end loop are substantially linear when constrained in the lumen of the delivery catheter. Upon deployment of the medical clip from the delivery catheter, the first tip extends from the first end loop and the second tip extends from the second loop in opposing directions approximately orthogonal to the longitudinal axis of the delivery catheter. The first tip may pass through a first piece of the patient tissue and the second tip may pass through the second piece of the patient tissue capturing the first piece of patient tissue and the second piece of patient tissue and drawing the first piece of patient tissue and the second piece of patient tissue together.

In an embodiment, the first end loop and the second end loop are resiliently biased to become co-planar with the tether loop when the first end loop and the second end loop are free from being constrained by the lumen of the delivery catheter.

In an embodiment, the tether loop, the first end loop and the second end loop each comprise at least one full revolution.

In an embodiment, the tether loop, the first end loop and the second end loop each comprise at least one-and-a-quarter revolutions.

In an embodiment, a system is disclosed for drawing together patient tissue. The system comprises a delivery catheter having a longitudinal axis and a lumen and a medical clip inserted in the lumen of the catheter. The medical clip comprises a tether loop, a first end loop having one end coupled to the tether loop and a first tip at an opposite end of the first end loop, the first end loop being resiliently biased to form a coil when the first end loop is free from being constrained by the lumen of the delivery catheter, and a second end loop having one end coupled to the tether loop and a second tip at an opposite end of the second end loop, the second end loop being resiliently biased to form a coil when the second end loop is free from being constrained by the lumen of the delivery catheter. Each of the first end loop and the second end loop are substantially linear when constrained in the lumen of the delivery catheter. Upon deployment of the medical clip from the delivery catheter, the first tip extends from the first end loop and the second tip extends from the second loop in opposing directions approximately orthogonal to the longitudinal axis of the delivery catheter. The first tip may pass through a first piece of the patient tissue and the second tip may pass through the second piece of the patient tissue capturing the first piece of patient tissue and the second piece of patient tissue and drawing the first piece of patient tissue and the second piece of patient tissue together.

In an embodiment, a method is disclosed for using a medical clip in a delivery catheter to draw together patient tissue. The method comprises the steps of positioning the delivery catheter in proximity of the patient tissue, and then deploying the medical clip, comprising a tether loop, a first end loop having one end coupled to the tether loop and a first tip at an opposite end of the first end loop, the first end loop being resiliently biased to form a coil when the first end loop is free from being constrained by the lumen of the delivery catheter, and a second end loop having one end coupled to the tether loop and a second tip at an opposite end of the second end loop, the second end loop being resiliently biased to form a coil when the second end loop is free from being constrained by the lumen of the delivery catheter, each of the first end loop and the second end loop being substantially linear when constrained in the lumen of the delivery catheter. The deploying step comprises the steps of pushing the medical clip out of an opening in a distal end of the delivery catheter, wherein the tips emerge from the delivery catheter in opposing directions relative to a longitudinal axis of the delivery catheter, then puncturing a first piece of the patient tissue with the first tip and puncturing a second piece of the patient tissue with the second tip, then capturing the first piece of patient tissue with the first end loop, and capturing the second piece of patient tissue with the second end loop, then drawing together the first piece of patient tissue and the second piece of patient tissue.

In an embodiment, a method of making a system for drawing together patient tissue is disclosed. The method comprises the steps of forming a medical clip comprising a tether loop, a first end loop having one end coupled to the tether loop and a first tip at an opposite end of the first end loop, the first end loop being resiliently biased to form a coil, and a second end loop having one end coupled to the tether loop and a second tip at an opposite end of the second end loop, the second end loop being resiliently biased to form a coil and inserting the medical clip in a delivery catheter. The inserting step comprises the steps of drawing the tether loop into the delivery catheter, drawing the first loop and the second loop into the catheter until the first tip and the second tip are contained within the catheter, wherein the first loop and the second loop straighten as they are drawn into the catheter.

In an embodiment, a medical clip adapted to be used with a delivery catheter having a longitudinal axis and a lumen is disclosed. The delivery catheter forms an opening having a first side and a second side opposite the first side and defining a major plane of the delivery catheter. The medical clip has a tether loop resiliently biased to form a coil having a spring force, a first end loop having one end coupled to the tether loop and a first tip at an opposite end of the first end loop, the first end loop being resiliently biased to form a coil when the first end loop is free from being constrained by the lumen of the delivery catheter, and a second end loop having one end coupled to the tether loop and a second tip at an opposite end of the second end loop, the second end loop being resiliently biased to form a coil when the second end loop is free from being constrained by the lumen of the delivery catheter. Each of the first end loop and the second end loop are substantially linear when constrained in the lumen of the delivery catheter. During deployment of the medical clip from the delivery catheter, the first tip exits the delivery catheter proximate the first side of the opening and curls in a first orthogonal direction relative to the major plane and the second tip exits the delivery catheter proximate the second side of the opening and curls in a second orthogonal direction relative to the major plane. At least a portion of the first end loop exits the delivery catheter proximate the second side of the opening and at least a portion of the second end loop exits the delivery catheter proximate the first side of the opening. The first tip may pass through a first piece of patient tissue in the first orthogonal direction relative to the deployment catheter and the second tip may pass through a second piece of patient tissue in the second orthogonal direction relative to the deployment catheter, capturing the first piece of patient tissue and the second piece of patient tissue. The spring force of the tether coil draws the first piece of patient tissue and the second piece of patient tissue toward each other by exerting a force in the second orthogonal direction on the first end loop and a force in the first orthogonal direction on the second end loop.

In an embodiment, upon deployment of the medical clip from the delivery catheter, the first tip extends from the first end loop and the second tip extends from the second loop in opposing directions approximately orthogonal to the longitudinal axis of the delivery catheter.

In an embodiment, a medical clip adapted to be used with a delivery catheter having a lumen and a lumen wall is disclosed. The delivery catheter forms an opening having a first side and a second side opposite the first side, the first side and the second side defining a major plane of the catheter. The medical clip has a central spring resiliently biased to form a loop in a compressed state, a first tissue capture spring having a first tip and coupled to a first end of the central spring, and a second tissue capture spring having a second tip and coupled to a second end of the central spring. When the medical clip is positioned in the lumen of the delivery catheter the central spring is maintained in an uncompressed state by the lumen wall and the first tip and the second tip are proximate the opening. The first tissue capture spring is resiliently biased such that the first tip exits the opening proximate the first side and wherein the second tissue capture spring is resiliently biased such that the second tip exits the opening proximate the second side. The central spring is resiliently biased such that at least a portion of the first tissue capture spring exits the opening proximate the second side and at least a portion of the second tissue capture spring exits the opening proximate the first side. When the central spring transitions from the uncompressed state to the compressed state the first tissue capture spring moves, at least in part, toward the first side and the second tissue capture spring moves, at least in part, toward the second side.

In an embodiment, the first tissue capture spring and the second tissue capture spring are maintained in an approximately linear state by the lumen wall.

In an embodiment, the first tissue capture spring moves, at least in part, in a first direction perpendicular to the major plane of the delivery catheter, the second tissue capture spring moves, at least in part, in a second direction perpendicular to the major plane of the delivery catheter opposite the first direction, and when the central spring transitions from the uncompressed state to the compressed state the first tissue capture spring moves, at least in part, toward the first side and the second tissue capture spring moves, at least in part, toward the second side.

In an embodiment, the first tissue capture spring and the second tissue capture spring are resiliently biased to become co-planar with the central spring when the first tissue capture spring and the second tissue capture spring are free from being constrained by the lumen of the delivery catheter.

In an embodiment, the central spring, the first tissue capture spring and the second tissue capture spring each comprise at least one full revolution.

In an embodiment, the central spring, the first tissue capture spring and the second tissue capture spring each comprise at least one-and-a-quarter revolutions.

In an embodiment, a medical clip system has a delivery catheter having a lumen and a lumen wall, the delivery catheter forming an opening having a first side and a second side opposite the first side, the first side and the second side defining a major plane of the catheter, and a medical clip. The medical clip has a central spring resiliently biased to form a loop in a compressed state, a first tissue capture spring having a first tip and coupled to a first end of the central spring, and a second tissue capture spring having a second tip and being coupled to a second end of the central spring. When the medical clip is positioned in the lumen of the delivery catheter the central spring is maintained in an uncompressed state by the lumen wall and the first tip and the second tip are proximate the opening. The first tissue capture spring is resiliently biased such that the first tip exits the opening proximate the first side and wherein the second tissue capture spring is resiliently biased such that the second tip exits the opening proximate the second side. The central spring is resiliently biased such that at least a portion of the first tissue capture spring exits the opening proximate the second side and at least a portion of the second tissue capture spring exits the opening proximate the first side, and when the central spring transitions from the uncompressed state to the compressed state the first tissue capture spring moves, at least in part, toward the first side and the second tissue capture spring moves, at least in part, toward the second side.

DRAWINGS

FIGS. 1a-d show a medical clip for drawing together patient tissue;

DESCRIPTION

It is often advantageous to capture and draw together pieces of tissue of a patient. Doing so may close and help wounds heal, or close defects in patient organs. Various capture and closure devices exist, but while such devices may be effective in certain situations and under certain conditions, they may be ineffective or disadvantageous in other conditions. Particularly in situations where the tissue to be drawn together is not readily accessible to personal manipulation, commonly known devices are often of limited use. The treatment of cardiac defects may be one such relatively common situation.

In order to treat cardiac defects such as a patent foramen ovale, it is desirable close the gap between flaps of cardiac tissue without having to experience the trauma and expense of open heart surgery. Accordingly, a medical clip and delivery system has been developed that may be inserted into the heart intravenously. Upon positioning the delivery system within the gap of the patent foramen ovale, a deployment system deploys the medical clip. The physical nature of the medical clip may capture and draw together the flaps of tissue of the patent foramen ovale, thereby reducing or closing the gap between the pieces of tissue altogether.

Figure 1A:
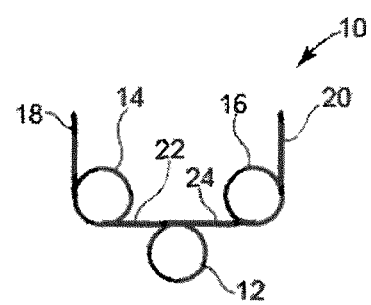

An embodiment of a medical clip for treating cardiac defects is illustrated in FIG. 1a. Clip 10 has tether loop 12, which, in an embodiment, acts as a central spring member. End loops 14, 16 are coupled to tether loop 12. In an embodiment, end loops 14, 16 act as tissue capture springs, the spring force of end loops 14, 16 aiding in the capture of tissue. Each end loop 14, 16 has an end 18, 20. In an embodiment, ends 18, 20 form sharpened tips. In the illustrated embodiment, end loops 14, 16 are coupled to tether loop 12 by way of separator segments 22, 24. In this embodiment, tether loop 12 is a coil of one full revolution, resulting in separator segments 22, 24 projecting straight out from tether loop 12 with respect to one another. In this embodiment, end loops 14, 16 are coils of one-and-a-quarter revolutions, resulting in ends 18, 20 extending from end loop 14, 16, respectively, at a ninety-degree angle with respect to separator segments 22, 24.

Figure 1B:
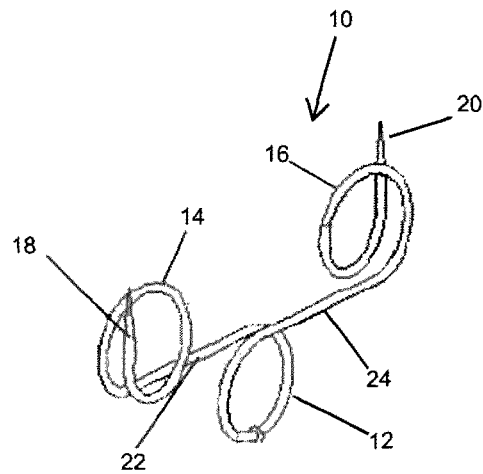

FIG. 1b shows a three-dimensional profile view of clip 10. The coiling of tether loop 12 places separator segment 22 relatively distal to separator segment 24 based on the perspective of FIGS. 1a and 1b. Likewise, the coiling of end loop 14 places end 18 relatively proximal to separator segment 22, and the coiling of end loop 16 places end 20 relatively distal to separator segment 24. In an embodiment, end 18 approximately shares a common plane with separator segment 24, while end 20 approximately shares a common plane with separator segment 22. In an alternative embodiment, end 18 is more proximal than separator segment 24 while end 20 is more distal than separator segment 22. In a further alternative embodiment, end 18 is more distal than separator segment 24 while end 20 is more proximal than separator segment 22.

Figure 1C:
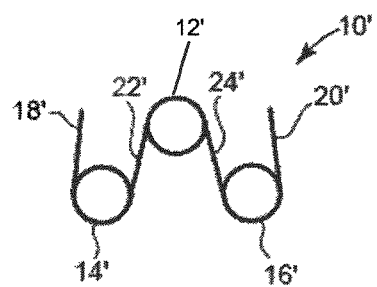

FIG. 1c shows an alternative embodiment of clip 10', in which tether loop 12' is a coil of greater than one full revolution, resulting in separator segments 22', 24' forming an angle to each other. Further, end loops 14', 16' are coils of between one-and-a-quarter and one-and-a-half revolutions, resulting in ends 18', 20' forming acute angles relative to separator segments 22', 24'.

Figure 1D:
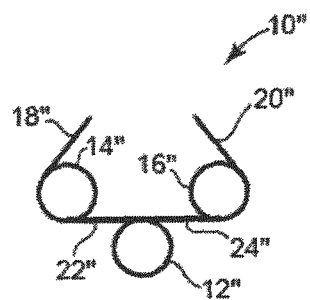

FIG. 1d shows a further alternative embodiment of clip 10", in which end loops 14", 16" are a coil of greater than one-and-a-quarter revolution, resulting in ends 18", 20" forming acute angles relative to separator segments 22", 24". Tether loop 12" remains one full revolution, resulting in separator segments 22", 24" projecting straight out from tether loop 12" with respect to one another.

In an embodiment, clip 10 is formed from a single length of material. In an embodiment, the material is a wire. In alternative embodiments, clip 10 may be formed from two or more lengths of wire. In such an embodiment, seams between lengths of wire may occur in any of tether loop 12, end loops 14, 16, and separator segments 22, 24.

Clip 10 may be formed from a variety of different materials. Any material may be used such that tether loop 12 and end loops 14, 16 may be resiliently biased to loop or coil when clip 10 has been deployed, provided the material is biocompatible or may be treated to make it biocompatible. In an embodiment, clip 10 is formed from the shaped memory alloy Nitinol. In alternative embodiments, biocompatible elastic material such as stainless steel may be utilized. Biocompatible super-elastic materials may also be utilized. Super-elastic materials could encompass super-elastic plastics and super-elastic metals. A super-elastic plastic generally is any material that has shape memory ability after shaped setting, e.g., materials described in the Massachusetts Institute of Technology, News Office article entitled "Intelligent Plastics Change Shape With Light, dated Apr. 13, 2005, authored by Elizabeth A. Thomson, which is hereby incorporated by reference in its entirety. A super-elastic metal is sometimes known as a shape memory alloy (also, smart metal, memory alloy or muscle wire) that remembers its shape and can be returned to that shape after being deformed, by applying heat to the alloy or removing an applied stress from the alloy. As the stress is removed, the material may undergo a martenisitic to austenitic conversion and spring back (e.g., self-revert) to its original or undeformed or undeflected configuration. When the shape memory effect is correctly harnessed, a super-elastic metal becomes a lightweight, solid-state alternative to a conventional actuator such as a hydraulic, pneumatic or motor-based system. In an embodiment, drawn filled tubes are filled with a super-elastic material or materials.

In a further alternative embodiment, spring-like bioabsorbable material may be utilized, which may result in clip 10 ultimately dissolving. Alternatively, a non-bioabsorbable material may be utilized to form clip 10, but the material may be coated with biological tissue, bioabsorbable polymer, a therapeutic substance or other substance which may be advantageously delivered to the treatment site concurrent with clip 10.

Figures 2, 3:
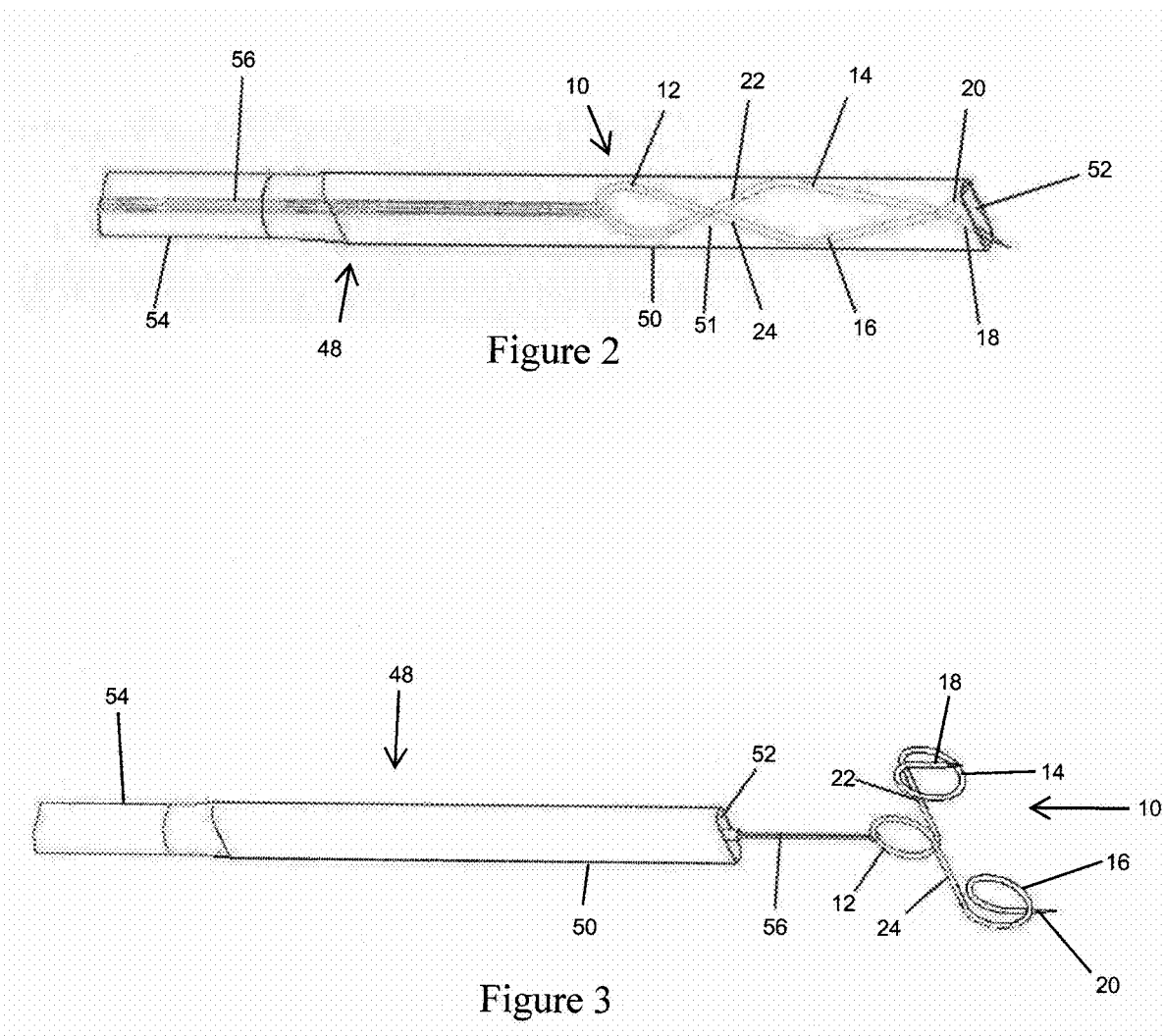
FIG. 2 shows an image of the medical clip of FIG. 1 positioned in a deployment catheter.
FIG. 3 shows the medical clip of FIG. 1 deployed from, but still coupled to the deployment catheter.

FIG. 2 illustrates an embodiment of clip 10 in an embodiment of a deployment catheter 48 having a sheath 50. To place clip 10 in sheath 50, tether loop 12 may be drawn into lumen 51 of sheath 50 by way of opening 52. As tether loop 12 is drawn in to sheath 50, each end loop 14, 16 is stressed by sheath 50, causing end loop 14, 16 to unwind and become relatively more linear when positioned in sheath 50. In the process, tether loop 12 transitions into an uncompressed state relative to being in a deployed mode, the uncompressed state tending to cause end loops 14, 16 to have a greater planar separation than when tether loop 12 is in its compressed state when deployed from the catheter. In an embodiment, end loops 14, 16 and separator segments 22, 24 do not become entirely linear, instead being substantially linear and forming a double-crossover pattern within sheath 50. Tether loop 12 uncoils to the extent that separator segments 22, 24 project in a common direction from tether loop 12, rather than in opposing directions. End 18, 20 of each tend loop 14, 16 may remain in proximity of the distal end of sheath 50.

Because of the spring force created by tether loop 12 and by end loops 14 and 16, clip 10 may exert lateral and horizontal forces within sheath 50. Because of the spring force of uncoiled end loops 14, 16, ends 18, 20 may tend to exert a lateral force within and contained by sheath 50. Likewise, the spring force of uncoiled end loops 14, 16 may tend to make uncoiled end loops 14, 16 themselves exert a horizontal force contained within sheath 50. In the case of both the horizontal and lateral forces, as clip 10 emerges from sheath 50, and sheath 50 no longer contains the forces, clip 10 may tend to adopt the resiliently biased shape shown in FIG. 1.

Sheath 50 may be coupled to catheter 54 to form deployment catheter 48. Catheter 54 may be utilized to guide sheath 50 into position to deploy clip 10. Catheter 54 may also be utilized to deploy clip 10. In an embodiment, catheter 54 has a deployment mechanism 56 in contact with bridge section 12. When deployment mechanism 56 pushes tether loop 12, clip 10 slides along sheath 50 until clip 10 has fully emerged from sheath 50.

FIG. 3 illustrates an embodiment of clip 10 fully emerged from sheath 50 but still attached to deployment mechanism 56. In the illustrated embodiment, tether loop 12 and end loops 14, 16 have returned to their resiliently biased looped state. In various embodiments of clip 10, dependent on the material from which clip 10 was made, end loops 14, 16 may coil within moments of emerging from sheath 50, or may require a lengthier amount of time to coil. In certain embodiments, end loops 14, 16 may, for a time, remain essentially straight even after tether loop 12 has emerged from sheath 50 due to the length of time required to coil. However, in such an embodiment, end loops 14, 16 will eventually coil after clip 10 has deployed from sheath 50.

Figure 4A:
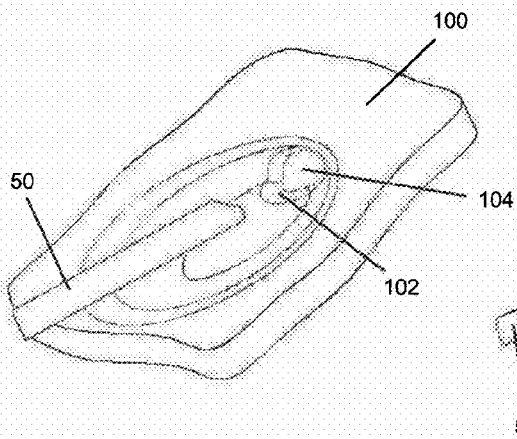
FIGS. 4a-4j illustrate the positioning and deployment of the medical clip of FIG. 1 for the treatment of a patent foramen ovale.
Figure 4B:
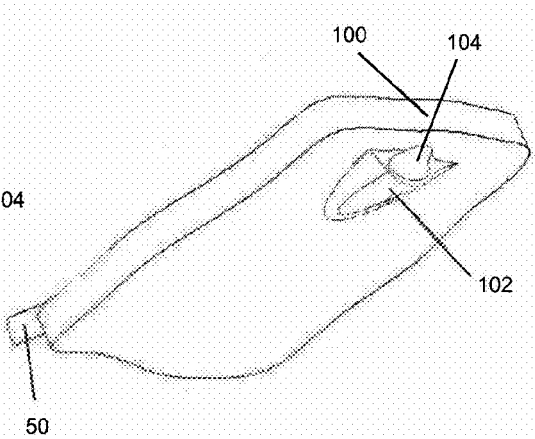
Figure 4C:
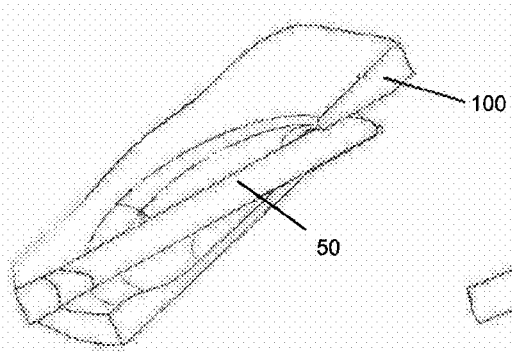
Figure 4D:
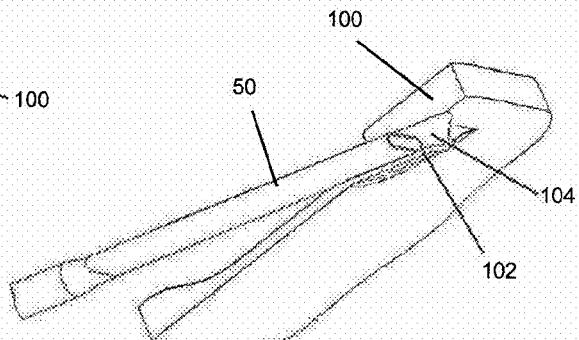
Figure 4E:
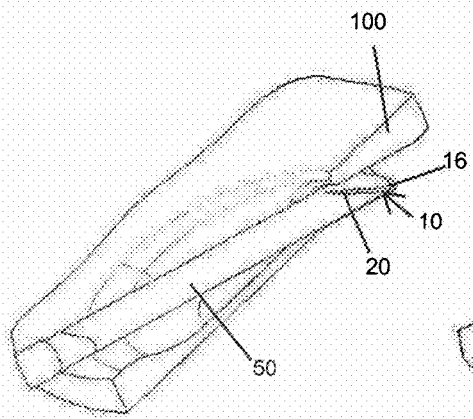
Figure 4F:
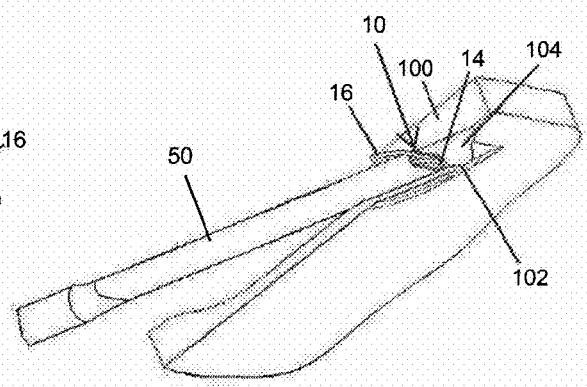
Figure 4G:
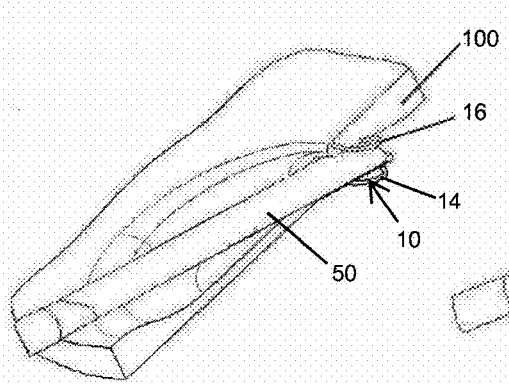
Figure 4H:
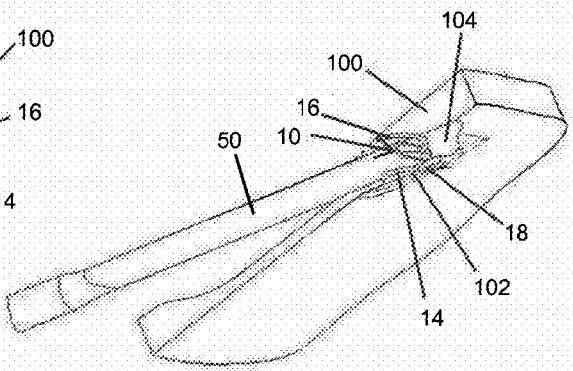
Figures 4I, 4J:
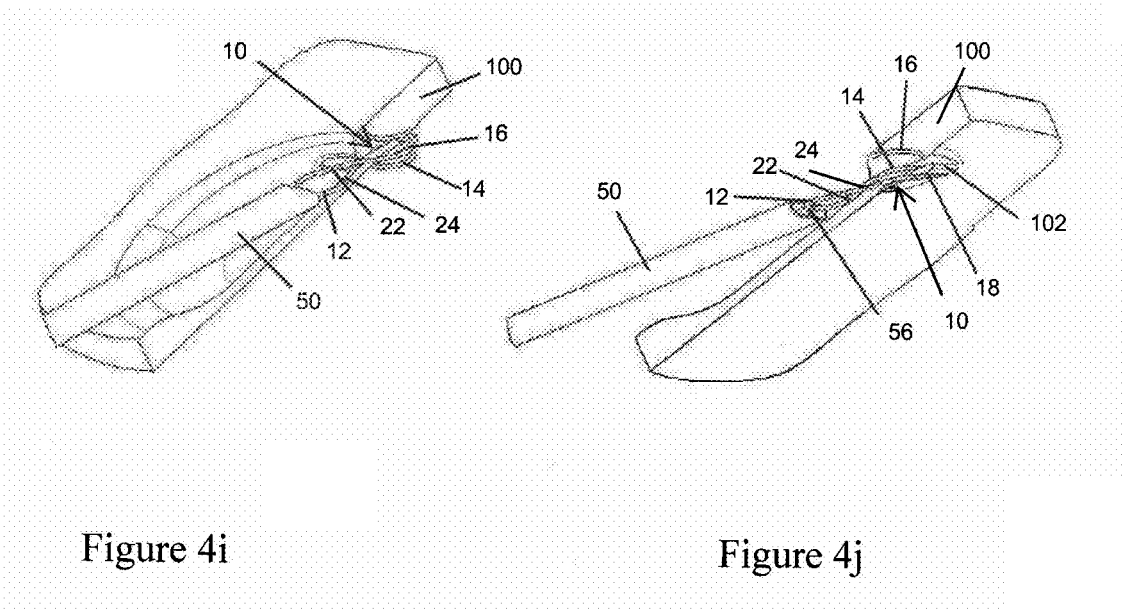
Figure 5:
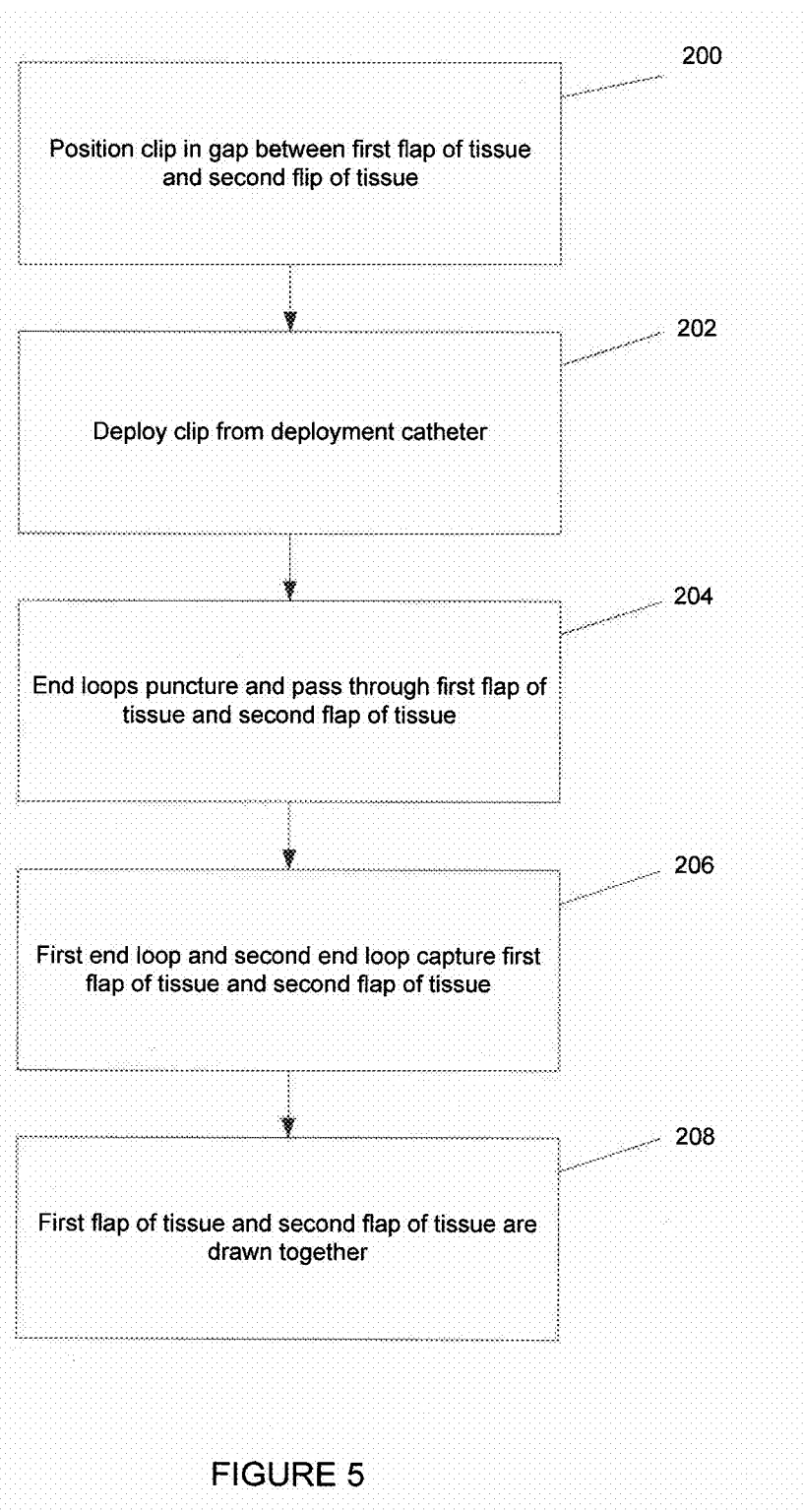
FIG. 5 is a flowchart for implanting a medical clip.
Figure 6A:
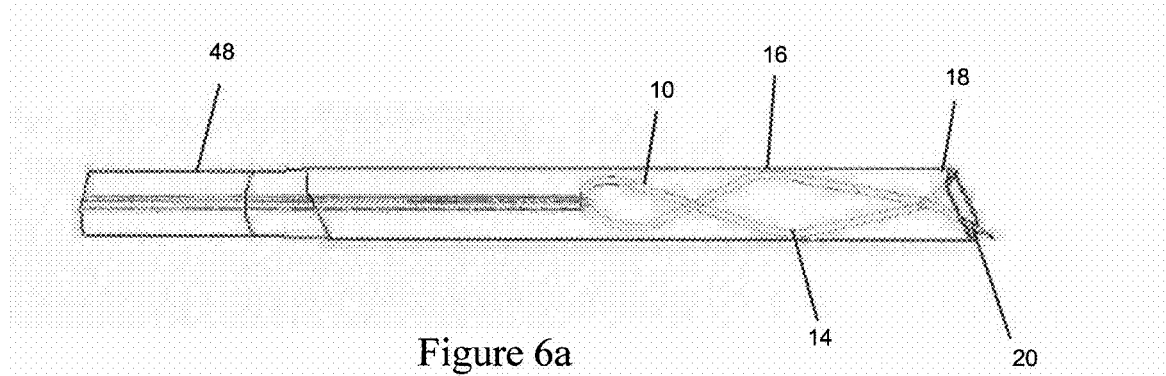
FIGS. 6a-6e illustrate the deployment of a system including the medical clip of FIG. 1 positioned in a deployment catheter.
Figure 6B:
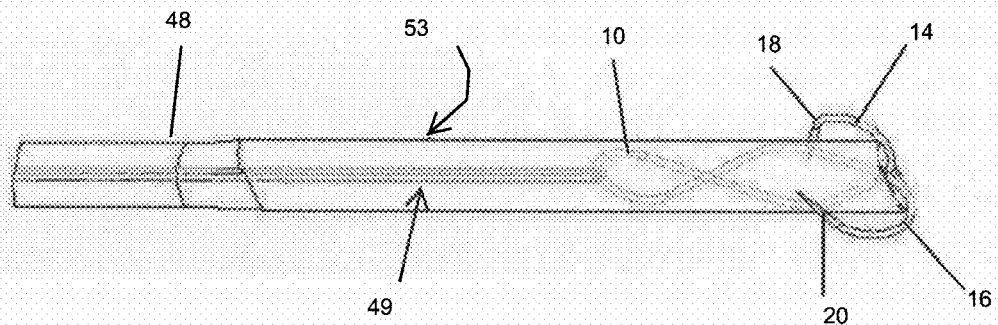
Figure 6C:
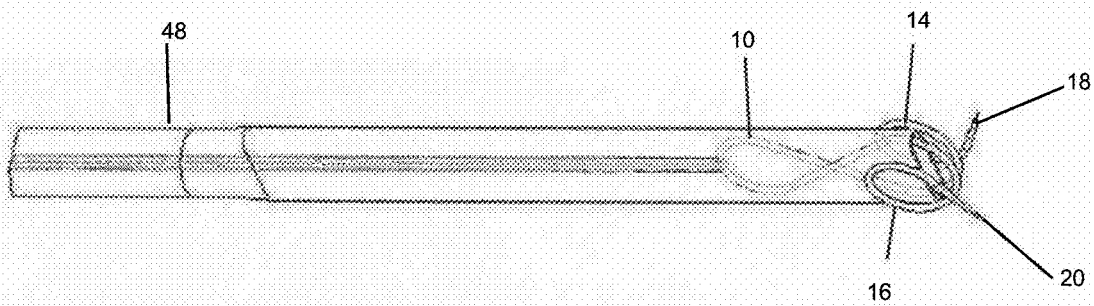
Figure 6D:
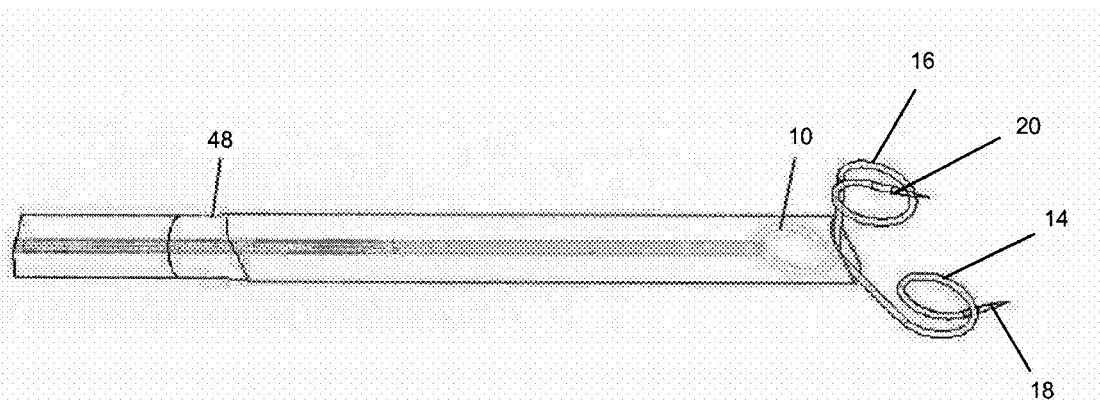
Figure 6E:
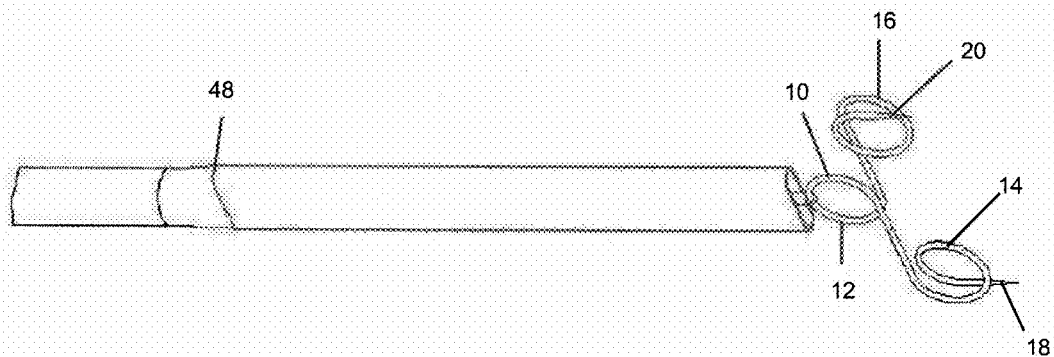

FIGS. 4a-4j and the flowchart of FIG. 5 illustrate a use of clip 10 and sheath 50 in the treatment of a patent foramen ovale. Opening 104 is between a first piece or flap of tissue 100 and a second piece or flap of tissue 102. Sheath 50 is shown approaching opening 104, or tunnel, of the patent foramen ovale (FIG. 4a). FIG. 4b shows a view of opening 104 from a left atrial perspective. FIG. 4c shows a sectioned view of the tunnel where sheath 50 is positioned (FIG. 5, 200) in opening 104 between a first flap or piece of tissue 100 and a second flap or piece of tissue 102 while clip 10 remains in sheath 50 with end loops 14, 16 uncoiled. FIG. 4d shows the same positioning from the left atrial perspective. As clip 10 is deployed (FIG. 5, 202) from sheath 50, end loops 14, 16 begin to coil (FIG. 4e). FIG. 4f shows the same positioning from the left atrial perspective. In an embodiment, deployment occurs by pushing medical clip 10 out of deployment catheter 48. The forward motion of clip 10 advancing out of opening 52 may cause end 18 to puncture (FIG. 5, 204) and pass through tissue 100 and end 20 to puncture and pass through tissue 102. As end loops 14, 16 complete coiling (FIGS. 4g and 4h), tissue 100 and tissue 102 are captured (FIG. 5, 206) and drawn together by the spring force of the separator segments 22, 24 being crossed, opposite of how separator segments 22, 24 were captured during loading, after end loops 14, 16 are fully deployed. The removal of sheath 50 exposes the tether loop 12 and may draw tissue 100 and tissue 102 completely together (FIG. 5, 208) and close opening 104 (FIGS. 4i and 4j). Alternatively, the completion of coiling may draw tissue 100 and tissue 102 nearly together though still leaving a reduced opening 104.

The treatment of other cardiac defects, such as atrial-septal defects ("ASD") and ventricular-septal defects ("VSD"), by the same steps illustrated above is also contemplated. In fact, any patient condition in which it is desirable to join or draw together two flaps of tissue may be effectively treated utilizing the steps illustrated in FIGS. 4a-4j. While the physical dimensions of clip 10 and delivery catheter 54 may need to change to reflect the different conditions, such as a wider opening 104 or tougher or thicker tissue 100, 102, the method of using clip 10 may remain unchanged.

The geometry of the components of clip 10 influence performance of clip 10. Relatively longer ends 18, 20 and separator segments 22, 24 and relatively greater diameter of end loops 14, 16 may allow for the treatment of a relatively larger opening 104, or result in greater depth of penetration of tissue 100, 102, perhaps increasing the likelihood of closing opening 104 altogether. A relatively longer length of separator segments 22, 24 in particular may result in an increased area of tissue 100, 102 that is drawn together, thereby increasing the tissue area brought together, aiding in the ultimate sealing of the foramen ovale. In situations where opening 104 is relatively narrow separator segments 22, 24 may be shortened or omitted altogether, with end loops 14, 16 coupled directly to tether loop 12. However, while longer separator segments 22, 24 may allow larger gaps to be closed, such longer separator segments 22, 24 may reduce the spring force, thereby the ability to completely close opening 104 between tissue 100, 102.

A relatively greater diameter of the material comprising end loops 14, 16 may increase the ability of end loops 14, 16 to hold tissue 100, 102 and decrease the likelihood of tissue 100, 102 slipping out of end loops 14, 16 during or after coiling. In an embodiment, the dimensions of end loops 14, 16 are approximately 0.090 inches and the diameter of the material forming clip 10 ranges from 0.008 inches to 0.018 inches.

FIG. 6 illustrates the deployment of clip 10 from deployment catheter 48. In an embodiment, initial deployment of clip 10 results in the emergence from delivery catheter 48 of ends 18 and 20 (FIG. 6a). In an embodiment, ends 18 and 20 emerge approximately orthogonal to a longitudinal axis of delivery catheter 48. However, emergence orthogonal to the longitudinal axis is not essential, and emergence in any direction consistent with the capturing of patient tissue 100, 102 is contemplated. As clip 10 emerges, end loops 14 and 16 emerge from delivery catheter 48 and begin to coil (FIG. 6b). Based on the perspective illustrated in FIG. 6b, end loop 16 coils in front 49 of delivery catheter 48 while end loop 18 coils in back 53 of delivery catheter 48. As end loops 14 and 16 complete coiling, ends 18 and 20 point, in an embodiment, approximately perpendicular to delivery catheter 48 and opposite to one another (FIG. 6c). In an alternative embodiment, ends 18 and 20 may not point in a perpendicular relationship with a major plane of delivery catheter 28 but may still be opposite one another. As clip 10 emerges further from delivery catheter 48, end loops 14 and 16 cross one another, based on the illustrated perspective (FIG. 6d). In other words, while in the illustrated perspective end loop 14 was initially above end loop 16, i.e., at the top of the drawing in FIG. 6b, by the time deployment illustrated in FIG. 6d is reached, end loop 16 is above end loop 14, i.e. at the bottom of the drawing in FIG. 6d. Deployment is completed when tether loop 12 emerges, as coupled to deployment mechanism 56 (FIG. 6e).

Figure 7:
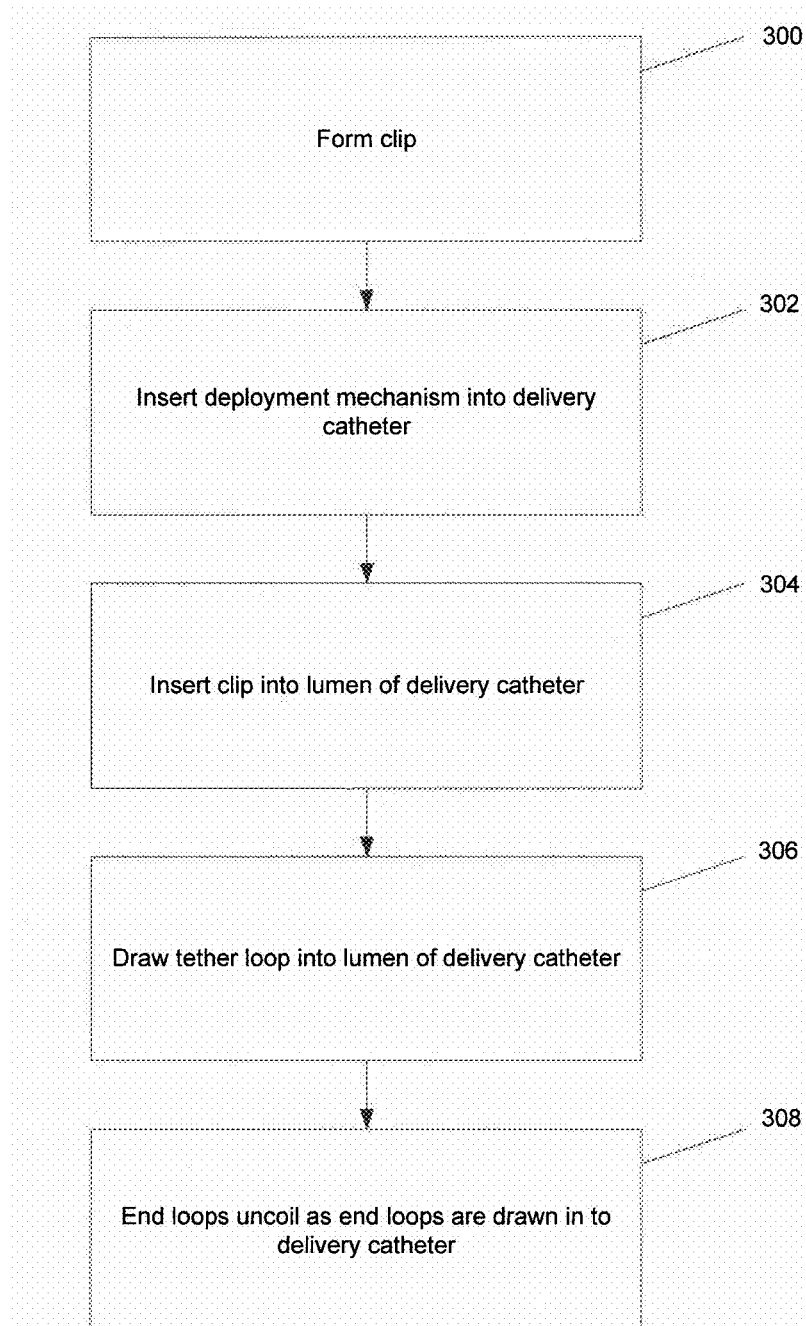
FIG. 7 is a flowchart for making a system including a medical clip positioned in a deployment catheter.

FIG. 7 is a flowchart of a method for making a system in which an embodiment of medical clip 10 is positioned in deployment catheter 48. In an embodiment, medical clip 10 is formed (300) bending a length of wire into the shape of medical clip 10. In an alternative embodiment, medical clip is formed by coupling end loops 14, 16 to tether loop 12. Deployment mechanism 56 is inserted (302) into lumen 51 (FIG. 2), such that when the deployment mechanism is used, medical clip 10 deploys out of lumen 51 and end loops 14, 16 coil. In embodiments where deployment mechanism 56 is coupled to medical clip 10, coupling deployment mechanism 56 to medical clip 10 may occur either before or after insertion (304) of medical clip 10 into delivery catheter 48. When coupling of deployment mechanism 56 to medical clip 10 occurs before insertion of medical clip 10, deployment mechanism 56 may be utilized to insert medical clip 10 into deployment catheter 48 by pulling medical clip into lumen 51. Insertion of medical clip 10 into deployment catheter 48 occurs by drawing (306) tether loop 12 into lumen 51. As tether loop 12 is drawn progressively further into lumen 51, end loops 14, 16 begin to uncoil (308) and follow tether loop 12 into lumen 51. The system may be complete when ends 18, 20 are enclosed within lumen 51. Alternatively, the system may be complete with ends 18, 20 still protruding from opening 52.

Thus, embodiments of the devices, system and methods of drawing patient tissue together are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A medical clip adapted to be used with a delivery catheter having a longitudinal axis and a lumen, comprising;
    a tether loop;
    a first end loop having one end coupled to said tether loop and a first tip at an opposite end of said first end loop, said first end loop being resiliently biased to form a coil when said first end loop is free from being constrained by said lumen of said delivery catheter;
    a second end loop having one end coupled to said tether loop and a second tip at an opposite end of said second end loop, said second end loop being resiliently biased to form a coil when said second end loop is free from being constrained by said lumen of said delivery catheter;
    each of said first end loop and said second end loop being substantially linear when constrained in said lumen of said delivery catheter; and
    wherein, upon initial deployment of said medical clip from said delivery catheter, said first tip extends from said first end loop and said second tip extends from said second loop in opposing directions approximately orthogonal to said longitudinal axis of said delivery catheter;
    and further wherein said medical clip is a wire continuously extending from said first tip to said second tip and when free of said lumen, continuous extension of said wire in a direction from said first tip to said second tip defines a first wind direction for said first end loop, a second wind direction opposite said first wind direction for said tether loop, and said first wind direction for said second end loop;
    whereby said first tip may pass through a first piece of said patient tissue and said second tip may pass through said second piece of said patient tissue capturing said first piece of patient tissue and said second piece of patient tissue and drawing said first piece of patient tissue and said second piece of patient tissue together.

2. The medical clip of claim 1 wherein said first end loop and said second end loop are resiliently biased to become co-planar with said tether loop when said first end loop and said second end loop are free from being constrained by said lumen of said delivery catheter.

3. The medical clip of claim 1 wherein said tether loop, said first end loop and said second end loop each comprise at least one full revolution.

4. The medical clip of claim 3 wherein said tether loop, said first end loop and said second end loop each comprise at least one-and-a-quarter revolutions.

5. A system for drawing together patient tissue, comprising:
    a delivery catheter having a longitudinal axis and a lumen; and
    a medical clip inserted in said lumen of said catheter, comprising:
        a tether loop;
        a first end loop having one end coupled to said tether loop and a first tip at an opposite end of said first end loop, said first end loop being resiliently biased to form a coil when said first end loop is free from being constrained by said lumen of said delivery catheter;
        a second end loop having one end coupled to said tether loop and a second tip at an opposite end of said second end loop, said second end loop being resiliently biased to form a coil when said second end loop is free from being constrained by said lumen of said delivery catheter;
        wherein relative to a continuous direction of extension of said medical clip from said first tip to said second tip, said coil of said first end loop has a counterclockwise winding, said tether loop has a clockwise winding, and said coil of said second end loop has a counterclockwise winding when said medical clip is free from being constrained by said lumen,
        each of said first end loop and said second end loop being substantially linear when constrained in said lumen of said delivery catheter; and
        wherein, upon initial deployment of said medical clip from said delivery catheter, said first tip extends from said first end loop and said second tip extends from said second loop in opposing directions approximately orthogonal to said longitudinal axis of said delivery catheter;
        whereby said first tip may pass through a first piece of said patient tissue and said second tip may pass through said second piece of said patient tissue capturing said first piece of patient tissue and said second piece of patient tissue and drawing said first piece of patient tissue and said second piece of patient tissue together.

6. The system of claim 5 wherein said first end loop and said second end loop are resiliently biased to become co-planar with said tether loop when said first end loop and said second end loop are free from being constrained by said lumen of said delivery catheter.

7. The system of claim 5 wherein said tether loop, said first end loop and said second end loop each comprise at least one full revolution.

8. The system of claim 7 wherein said tether loop, said first end loop and said second end loop each comprise at least one-and-a-quarter revolutions.

9. A medical clip adapted to be used with a delivery catheter having a longitudinal axis and a lumen, said delivery catheter forming an opening having a first side and a second side opposite said first side and defining a major plane of said delivery catheter, comprising;
    a tether loop resiliently biased to form a coil having a spring force;
    a first end loop having one end coupled to said tether loop and a first tip at an opposite end of said first end loop, said first end loop being resiliently biased to form a coil when said first end loop is free from being constrained by said lumen of said delivery catheter;
    a second end loop having one end coupled to said tether loop and a second tip at an opposite end of said second end loop, said second end loop being resiliently biased to form a coil when said second end loop is free from being constrained by said lumen of said delivery catheter;
    each of said first end loop and said second end loop being substantially linear when constrained in said lumen of said delivery catheter; and
    wherein said medical clip is configured such that:
        during an initial stage of deployment of said medical clip from said delivery catheter, said first tip exits said delivery catheter proximate said first side of said opening and curls in a first orthogonal direction relative to said major plane and said second tip exits said delivery catheter proximate said second side of said opening and curls in a second orthogonal direction relative to said major plane; and during an intermediate stage of deployment of said medical clip from said delivery catheter, at least a portion of said first end loop exits said delivery catheter proximate said second side of said opening and at least a portion of said second end loop exits said delivery catheter proximate said first side of said opening;

wherein said first tip may pass through a first piece of patient tissue in said first orthogonal direction relative to said deployment catheter and said second tip may pass through a second piece of patient tissue in said second orthogonal direction relative to said deployment catheter, capturing said first piece of patient tissue and said second piece of patient tissue; and wherein said spring force of said tether coil draws said first piece of patient tissue and said second piece of patient tissue toward each other by exerting a force in said second orthogonal direction on said first end loop and a force in said first orthogonal direction on said second end loop.

10. The medical clip of claim 9 wherein, upon deployment of said medical clip from said delivery catheter, said first tip extends from said first end loop and said second tip extends from said second loop in opposing directions approximately orthogonal to said longitudinal axis of said delivery catheter.

11. A medical clip adapted to be used with a delivery catheter having a lumen and a lumen wall, said delivery catheter forming an opening having a first side and a second side opposite said first side, said first side and said second side defining a major plane of said catheter, comprising:

a central spring resiliently biased to form a loop in a compressed state;

a first separator segment extending from a first end of said central spring;

a first tissue capture spring having a first tip and being coupled to said first separator segment;

a second separator segment extending from a second end of said central spring;

a second tissue capture spring having a second tip and being coupled to said second separator segment;

wherein relative to a line passing through said first and second separator segments, said first and second tissue capturing springs project away from said line in a first direction and said central spring projects away from said line in a second direction opposite said first direction;

wherein when said medical clip is positioned in said lumen of said delivery catheter said central spring is maintained in an uncompressed state by said lumen wall and said first tip and said second tip are proximate said opening;

wherein said first tissue capture spring is resiliently biased such that said first tip exits said opening proximate said first side and wherein said second tissue capture spring is resiliently biased such that said second tip exits said opening proximate said second side; and wherein said central spring is resiliently biased such that at least a portion of said first tissue capture spring between said first tip and said first separator segment exits said opening proximate said second side and at least a portion of said second tissue capture spring between said second tip and said second separator segment exits said opening proximate said first side, and wherein when said central spring transitions from said uncompressed state to said compressed state said first tissue capture spring moves, at least in part, toward said first side and said second tissue capture spring moves, at least in part, toward said second side.

12. The clip of claim 11 wherein said first tissue capture spring and said second tissue capture spring are maintained in an approximately linear state by said lumen wall.

13. The clip of claim 11:
wherein said first tissue capture spring moves, at least in part, in a first direction perpendicular to said major plane of said delivery catheter;

wherein said second tissue capture spring moves, at least in part, in a second direction perpendicular to said major plane of said delivery catheter opposite said first direction; and wherein when said central spring transitions from said uncompressed state to said compressed state said first tissue capture spring moves, at least in part, toward said first side and said second tissue capture spring moves, at least in part, toward said second side.

14. The clip of claim 11 wherein said first tissue capture spring and said second tissue capture spring are resiliently biased to become co-planar with said central spring when said first tissue capture spring and said second tissue capture spring are free from being constrained by said lumen of said delivery catheter.

15. The clip of claim 11 wherein said central spring, said first tissue capture spring and said second tissue capture spring each comprise at least one full revolution.

16. The clip of claim 15 wherein said central spring, said first tissue capture spring and said second tissue capture spring each comprise at least one-and-a-quarter revolutions.

17. A medical clip system, comprising:
a delivery catheter having a lumen and a lumen wall, said delivery catheter forming an opening having a first side and a second side opposite said first side, said first side and said second side defining a major plane of said catheter;

a medical clip, comprising:
a central spring resiliently biased to form a loop in a compressed state;
a first tissue capture spring having a first tip and being coupled to a first end of said central spring;
a second tissue capture spring having a second tip and being coupled to a second end of said central spring;
wherein said system is configured such that:
in a pre-deployment stage when said medical clip is positioned in said lumen of said delivery catheter, said central spring is maintained in an uncompressed state by said lumen wall and said first tip and said second tip are proximate said opening;
in an initial stage of deployment said first tissue capture spring is resiliently biased such that said first tip exits said opening proximate said first side and wherein said second tissue capture spring is resiliently biased such that said second tip exits said opening proximate said second side;
in an intermediate stage of deployment said central spring is resiliently biased such that at least a portion of said first tissue capture spring exits said opening proximate said second side and at least a portion of said second tissue capture spring exits said opening proximate said first side; and
in a final stage of deployment when said central spring transitions from said uncompressed state to said compressed state said first tissue capture spring moves more proximate said second side and said second tissue capture spring moves more proximate said first side.

18. The system of claim 17 wherein said first tissue capture spring and said second tissue capture spring are maintained in an approximately linear state by said lumen wall.

19. The system of claim 17:
wherein said first tissue capture spring moves, at least in part, in a first direction perpendicular to said major plane of said delivery catheter;
wherein said second tissue capture spring moves, at least in part, in a second direction perpendicular to said major plane of said delivery catheter opposite said first direction; and
wherein when said central spring transitions from said uncompressed state to said compressed state said first tissue capture spring moves, at least in part, toward said first side and said second tissue capture spring moves, at least in part, toward said second side.

20. The system of claim 17 wherein said first tissue capture spring and said second tissue capture spring are resiliently biased to become co-planar with said central spring when said first tissue capture spring and said second tissue capture spring are free from being constrained by said lumen of said delivery catheter.

21. The system of claim 17 wherein said central spring, said first tissue capture spring and said second tissue capture spring each comprise at least one full revolution.

22. The system of claim 21 wherein said central spring, said first tissue capture spring and said second tissue capture spring each comprise at least one-and-a-quarter revolutions.

* * * * *